United States Patent
Gilbert

(10) Patent No.: US 9,427,187 B2
(45) Date of Patent: Aug. 30, 2016

(54) SYSTEM FOR ANALYSING THE SKIN AND ASSOCIATED METHOD

(75) Inventor: Jerome Gilbert, Levallois-Perret (FR)

(73) Assignee: L'OREAL, Paris (FR)

(*) Notice: Subject to any disclaimer, the term of this patent is extended or adjusted under 35 U.S.C. 154(b) by 1154 days.

(21) Appl. No.: 13/173,805

(22) Filed: Jun. 30, 2011

(65) Prior Publication Data

US 2012/0172685 A1 Jul. 5, 2012

(30) Foreign Application Priority Data

Jan. 4, 2011 (FR) ...................................... 11 00026
May 20, 2011 (FR) ...................................... 11 01549

(51) Int. Cl.
*A61B 5/00* (2006.01)
*A61B 10/00* (2006.01)

(52) U.S. Cl.
CPC ............. *A61B 5/441* (2013.01); *A61B 5/0013* (2013.01); *A61B 5/0059* (2013.01); *A61B 5/0077* (2013.01); *A61B 5/442* (2013.01); *A61B 5/443* (2013.01); *A61B 5/444* (2013.01); *A61B 5/445* (2013.01); *A61B 5/6833* (2013.01); *A61B 5/6888* (2013.01); *A61B 5/6898* (2013.01); *A61B 10/0035* (2013.01); *A61B 5/0051* (2013.01); *A61B 2560/0223* (2013.01); *A61B 2562/08* (2013.01); *A61B 2576/02* (2013.01)

(58) Field of Classification Search
CPC ............ A61B 10/0035; A61B 5/0059; A61B 5/0077; A61B 5/411; A61B 5/441; A61B 5/442; A61B 5/443; A61B 5/444; A61B 5/6888; A61B 5/6898
See application file for complete search history.

(56) References Cited

U.S. PATENT DOCUMENTS

| | | | |
|---|---|---|---|
| 2,657,611 A * | 11/1953 | Borth | 356/394 |
| 4,911,544 A | 3/1990 | Walsh | |
| 6,028,700 A * | 2/2000 | Fraenkel | 359/408 |
| 6,032,071 A * | 2/2000 | Binder | 600/476 |
| 6,251,070 B1 * | 6/2001 | Khazaka | 600/306 |
| 6,792,137 B2 * | 9/2004 | Kenet | 382/128 |
| 6,993,167 B1 * | 1/2006 | Skladnev et al. | 382/128 |
| 7,522,825 B2 * | 4/2009 | Kenet | 396/14 |
| 2004/0125996 A1 * | 7/2004 | Eddowes et al. | 382/128 |
| 2004/0258288 A1 * | 12/2004 | Kenet | 382/128 |
| 2006/0092315 A1 | 5/2006 | Payonk et al. | |
| 2008/0194928 A1 * | 8/2008 | Bandic et al. | 600/306 |
| 2009/0185727 A1 | 7/2009 | Beckmann et al. | |

(Continued)

FOREIGN PATENT DOCUMENTS

| | | |
|---|---|---|
| EP | 1433418 A1 | 6/2004 |
| WO | 0124994 A1 | 4/2001 |
| WO | 2008064120 A2 | 5/2008 |

OTHER PUBLICATIONS

French Search Report, dated Aug. 12, 2011, in FR 1100026.

*Primary Examiner* — Navin Natnithithadha
(74) *Attorney, Agent, or Firm* — Young & Thompson

(57) ABSTRACT

A system for analyzing at least one characteristic of the skin (1) and by extension hair, via optics (7, 4) and image processing (4, 5) elements notably include a consumer electronics device (4). The method for analyzing at least one characteristic of the skin notably includes a step wherein at least one digital image is acquired via a consumer electronics device. According to a first aspect, the method notably aims at applications in the field of cosmetics or that of skin cancer screening, and according to a second aspect in the field of assisting with diagnosis of allergies.

29 Claims, 12 Drawing Sheets

(56) References Cited

U.S. PATENT DOCUMENTS

2010/0063402 A1\* 3/2010 Sheinis ................. 600/476
2010/0309300 A1 12/2010 Chhibber et al.
2011/0301441 A1\* 12/2011 Bandic et al. ............... 600/306
2012/0307032 A1\* 12/2012 Gomi et al. .................. 348/77

\* cited by examiner

SYSTEM FOR ANALYSING THE SKIN AND ASSOCIATED METHOD

TECHNICAL FIELD

The invention is located in the field of analysis of characteristics of the skin and by extension of that of hair. According to a second aspect, the invention is located in the field of help to diagnosis of allergies.

BACKGROUND OF THE INVENTION

Professional solutions are known for analyzing the skin from specialized stations generally comprising a microscope-camera probe equipped with a light source, this assembly being used as a peripheral of a computer and used for image analysis by means of a suitable software package executed on the local computer. Self-contained versions of a skin analyzer are also known, certain appliances are intended for dermatologists, others are directed to the field of cosmetics. Some of these professional appliances further use specialized sensors for measuring the humidity level and/or the flexibility of the skin.

SUMMARY OF THE INVENTION

The present invention is located in the field of the analysis of skin characteristics. The skin in the sense of the invention comprising the whole of the constituents, appendices and functionalities of the organ. It is thus provided for example that the invention be used for analysis of hair. Applications of the invention are provided for prescribing cosmetics and/or actives and/or treatments depending on at least one characteristic of the skin. Applications of the invention are also provided for screening skin cancer. Indeed, provision is made for using the invention within the scope of detecting melanoma. Moles may thus be monitored on the basis of the following actions: periodic acquisition of a digital image and storage in memory of the correspondent information, automatic comparison of the development between image shots, computation of the development rate and generation of alert(s) urging consultation of specialized physicians, possible automatic making of appointments with utilization of geolocalization and of the emergency level related to the significance of the detected problem. Indeed, a melanoma may develop very rapidly and jeopardize the life of the person. The usual frequency of follow-up visits at a dermatologist is generally too low with regard to the incurred risk. With the invention, persons at risk may keep watch on themselves as many times as required without the constraint of taking an appointment and of the difficulty in finding an early date and this with less cost for health funding systems.

Moreover, the increase in the number of mobile telephones is phenomenal worldwide with an average equipment rate of persons, for all countries, which is presently of the order of 60% globally and which is close to 80% in most developed countries. Most of the recent versions of mobile telephones have an onboard digital camera function. Further, the segment of smartphones capable of executing specific applications, drawn by the symbolic series of the Apple iPhones (registered trademarks), by appliances compatible with the Android system of Google (registered trademarks) or further by the Blackberrys of Research in Motion (registered trademarks), is strongly growing. Other types of electronic appliances equipped with an image acquisition function are available to the general public and used alone or with accessories or further combined, are capable of applying the invention. For example these are digital tablets such as the Apple iPad (registered trademarks), personal media players such as certain Apple iPods (registered trademarks), portable computers with an incorporated or added camera, fixed computers with a webcam added, digital still and video cameras, connected television sets with an incorporated or added camera, etc., The invention provides a system for analyzing at least one characteristic of the skin by means falling within optics and image processing.

The system according to the invention comprises:
 a consumer electronics device, capable of acquiring at least one image by digital means and capable of producing data in relation with said at least one acquired image; and
 means for processing said data in relation with said at least one acquired image with the purpose of producing information in relation with at least one characteristic of the skin.

The invention provides that the system further comprises: means for producing optical magnification of the image.

Within the scope of a first alternative embodiment, the invention provides that the means for producing optical magnification of the image comprise:
 means for sharpening the image upon acquiring an image at a shorter distance than the shortest possible distance for which said consumer electronics device was designed; and
 means for temporarily attaching said image-sharpening means on said consumer electronics device so that the image-sharpening means are suitably placed with respect to the objective of the consumer electronics device.

Within the scope of a second alternative embodiment, the invention provides that the means for producing optical magnification of the image comprise:
 means for sharpening the image independently of the distance at which is found the objective of the consumer electronics device used for acquiring the image; and
 means for temporarily maintaining the image-sharpening means in a functional position on the skin.

By analysis of at least one characteristic of the skin is meant any method with which quantitative or qualitative information may be produced in connection with at least one characteristic of the skin. However it should be noted that the invention by applying means such as databases allowing characteristics to be linked together, intends to produce information on a characteristic of interest of the skin which is not the one on which the analysis was dealing with, strictly speaking.

By characteristic of the skin is meant any physical, chemical or biological characteristic of the skin, the analysis of which is useful in the field of application of the invention. The skin is understood in its widest definition including the whole of the tissues and constituents of this organ including skin appendages such as nails, individual hairs, and hair as well as the ecosystem of the skin, any product in relation with the skin and any outward pathological sign of the skin.

By image processing is meant any processing of the data resulting from the acquisition of the image by digital means, for example, any algorithm applied to the pixels of the image extracted from the file resulting from the acquisition of a digital photograph. In the invention, provision is also made for applying processing operations to frames of a video stream stored as a file or being captured.

By consumer electronics device capable of acquiring at least one image by digital means and capable of producing data in connection with said at least one acquired image is meant any appliance accessible to the general population, which comprises means allowing digital images to be captured one by one, as a sequence or as a continuous stream. In other words, this is any appliance which was not specifically designed for analyzing the skin as intended for professionals. Of course, it is provided that the solutions of the invention may also be used by professionals. These are for example electronic appliances comprising a digital still or video camera function. Consumer electronics devices which may be used within the scope of the invention are for example simple cell phones, smartphones, digital tablets, personal media players, microcomputers or television sets equipped with a digital still or video camera function. However there is no departure from the invention in the case of assembling a plurality of consumer electronics devices in order to apply the functions required for the invention. For example, provision is made for the possibility of using a webcam connected to a microcomputer or to a tablet or further a digital still or video camera for acquiring the images within the scope of a first acquisition step without any image processing which is completed by the use of a digital tablet or of a microcomputer in order to handle a local image processing step and/or a step for transmitting information towards a server via a network in order to perform remote image processing operations.

Within the scope of said first alternative embodiment, by image-sharpening means during an image acquisition at a shorter distance than the shortest possible distance for which said consumer electronics device was designed is meant any optical device interposed between the objective of the electronic appliance and the object of the image acquisition, any means applied in the form of at least one software package, and any combination of at least one optical device and at least one software package. Conventionally in the following of this document, a device according to the invention or an image-sharpening device will designate any application in a hardware form of means for sharpening the image during an image acquisition at a shorter distance than the shortest possible distance for which the said consumer electronics device was designed. This may for example be a simple convergent lens or a group of lenses placed in front of the objective. It is provided in the invention that the applied lenses be made in glass or in a plastic material of optical quality molded in order to reduce the costs. In certain alternative embodiments most particularly intended for cosmetics, optics are provided for sharpening the image with a relatively large field depth so as to allow sharp shots of skin surfaces of interest which are not planar such as for example the contour of the eye, the eyelids, the corner of the mouth, the forehead, the neck. It is provided that the image-sharpening means during an image acquisition at a shorter distance than the shortest possible distance for which said consumer electronics device was designed, be applied as at least one software package for example in the case of consumer electronics devices, for which the minimum automatic focusing distance is blocked at a too large distance relatively to the needs of the invention. It happens that manufacturers of electronic devices block the capability of taking photographs with their devices before the occurrence of visible distortions in the image even though these devices may technically acquire images at shorter distances. In non-artistic applications like those of the invention, the distortions appearing at a short distance are not bothersome and may be corrected by image processing. In such cases, depending on the type of consumer electronics device, a specific application software package or a new version of embedded software (firmware) allows unblocking of the distance limitations applied by the manufacturers of the appliances. It should be noted that such limitations on the image acquisition distance in consumer electronics devices are only generally applied in a photographic mode and this limitation is not applied in the video mode which is often proposed. This being the case, the photographic mode will be preferred when this will be possible as it generally allows acquisitions of images having greater resolution than in the associated video mode.

By means for temporarily attaching said image-sharpening means onto said consumer electronics device, any attachment means allowing adaptation to the conformation of said electronic appliance so as to align the optical axis of the image-sharpening means and of the objective of the electronic appliance. The attachment means are further provided for observing the integrity of the electronic appliance. For example provision is made for the use of a so-called repositionable adhesive film i.e. which adheres to the surface of the appliance but which may be detached by applying a small force without damaging the surface of the appliance. Advantageously, the application of a suitable adhesion primer on the corresponding surface of the image-sharpening means and then the laying of a peelable protective film on the external surface of the repositionable adhesive film during manufacturing gives the possibility of obtaining both permanent adhesion of the film on the image-sharpening means and adhesion of the repositionable type on the surface intended to be in contact with the external surface of the electronic appliance. Provision is also made for means for temporarily attaching said image-sharpening means on said consumer electronics device, which do not use any adhesive but use entirely mechanical means. In certain alternatives, mechanical means are provided which are adjustable for adapting said image-sharpening means to a plurality of consumer electronics device versions. Such mechanical means use suitable cutouts in elements of the image-sharpening means, these means then being firmly maintained secured to the electronic appliance by frictional forces resulting from close assembly. Provision is also made for the use of at least one bracelet in elastic material in certain particularly economical alternatives. In other alternatives, it is provided that said image-sharpening means be mechanically designed in order to be perfectly adapted to a single version or to a family of particularly widespread consumer electronics devices, for example a design dedicated to one or several <<iPhone>> versions or to one or more <<iPod>> versions (registered trademarks of Apple Computer) equipped with a camera or further to one or more <<Blackberry>> (registered trademark of Research in Motion) versions.

Within the scope of this second alternative embodiment, by means for sharpening the image independently of the distance at which is found the objective of the consumer electronics device used for acquiring the image, are meant optical means which show the magnified and sharp image of the skin surface and annex elements according to the invention which are included in the image if necessary. The optical means are laid out so that the sharpness of the image provided by the device does not change according to the distance at which the objective of the electronic appliance is found. The ratio of the surfaces of the image of interest visible on the main external face of the device according to the invention only changes relatively to the remaining surface of the acquired image when the distance between the device and the electronic device is changed. This second alternative assumes optical components with a relatively large surface so that the size of the image visible by the electronic appliance in the global image to be acquired comprises a sufficient number of pixels for making it suitable for image processing operations according to the invention. In practice, an image of the order of 3 centimeters×5 centimeters is suitable for acquisition by most electronic appliances. Fresnel lenses are the preferred optical components for applying this alternative of the invention in that with them it is possible to make lenses of large surface area, both performing within the scope of the invention and with small thickness. Fresnel lenses provide additional advantages of being flexible and of low cost when they are made in plastic material sheets of optical quality. This second alternative embodiment of the device according to the invention further provides the advantage of providing an image visible to the naked eye without it being necessary to resort to monitoring means of an electronic appliance. Within the scope of the application to skin cancer detection, this alternative may under certain conditions dispense the user with acquiring one or more global images of a larger portion of the body for localizing moles or followed lesions. This is so because the image from the means of the invention is naturally comprised in an image of a larger skin surface which generally allows localization of the location of the body where it is located.

By means for temporarily maintaining the image-sharpening means in a functional position on the skin are meant any means by which the hands of the user may be freed in order to maintain the device in a position suitable for image acquisition. The user may thus advantageously use both of his/her hands for handling the electronic appliance with the purpose of acquiring the image. For example, consumable means are provided comprising a repositionable adhesive film on both sides. The adhesive is advantageously compatible with application on the skin. This technical solution is particularly preferred within the scope of lightweight and low cost means using Fresnel lenses made in plastic sheets. The thereby formed device may thus be held without any risk of falling, on a vertical skin surface. However there is no departure from the scope of the invention when the effect of gravity is used for maintaining the device in position. The device is then simply laid on the skin surface of interest. It is the responsibility of the person to adopt the suitable position taking into account the localization of the skin surface of interest so that the device is maintained in position under the effect of gravity.

The system according to the invention further provides that said image-sharpening means comprise means for providing high optical magnification of the image. The interposition of image-sharpening means the image during an image acquisition at a shorter distance than the shortest distance possible for which the consumer electronics device was designed, naturally induces a first optical magnification level relatively to the rated characteristics of the device by modification of the distance ratios. Further, the resolution of the cameras aboard consumer electronics devices increases at each generation of appliances with equal sensor surface area or even with more reduced sensor surface area. This results in that the natural magnification applying by interposition of the image-sharpening means is generally sufficient for applying the image processing operations according to the invention and for obtaining the expected results therefrom. In certain cases however provision is made for increasing the natural magnification provided by the image-sharpening means by adding additional optical means allowing high magnification associated with an optical aberration level compatible with the image processing operations according to the invention. For example, high optical magnification is required for analyzing hair according to the invention.

The system according to the invention provides that the means for producing optical magnification of the image further comprise means for transforming the expression of at least one physical, chemical or biological characteristic of the skin so as to allow said at least one physical, chemical or biological characteristic skin to be appreciated by image processing. This technical characteristic is particularly useful in the case of applications of the invention in the field of cosmetics. For example the invention provides the use of chemical reagents which change color according to a chemical characteristic such as acidity, the amount of sebum or further a physical characteristic such as the humidity level at the surface. Provision is also made for reagents capable of changing color depending on biological characteristics such as in relation with the type of microorganisms colonizing the analyzed skin surface, the knowledge of which may be exploited in the field of cosmetics. Said reagents are placed on a support which is both in contact with the skin to be analyzed and in the plane of the image acquired by the electronic device. More advantageously, provision is made for the support of said reagents to be firmly secured to said image-sharpening means. It is also provided that on the support, a code is marked, appearing in the plane of the image acquired by the electronic appliance in order to allow image processing algorithms to determine the reagent used for suitably interpreting the relevant image elements. It is also provided that the support bearing the reagents is a single-use consumable protected from any contact with the outside environment by means which are removed by the user before using the device. According to alternative embodiments, the support bearing the reagents is removably and replaceably mounted on said image-sharpening means or to is an integral part of said means. In another alternative embodiment for measuring the flexibility of the skin which is a characteristic of interest in the field of cosmetics, it is provided that the expression of this physical characteristic be transformed into a modification of pixels in the image capable of allowing it to be appreciated by image processing. For example, provision may be made for using pins firmly secured to the portion of the image-sharpening means, which are in contact with the skin and which locally cause a deformation of the observable lines characterizing the relief of the skin when a force is applied vertically or rotatably. Suitable image processing algorithms are provided for transforming the observed deformations into an appreciation of the elasticity of the skin. Provision is also for example made for vibrating the pins so as to locally induce blurring in the image of the relief of the skin, the observable extent of which depends on the elasticity of the skin. It should be noted that in the case when the electronic appliance is a smartphone, it is advantageous to apply an application capable of driving the vibrator of the telephone which is mechanically firmly secured to the image-sharpening means and to therefore be able to appreciate the elasticity of the skin without adding any specific hardware means.

The system according to the invention provides that the means for producing optical magnification of the image further comprise means for allowing the user to enter at least one piece of information into the image. In the invention, provision is made for means such as for example a medium on which the user may enter pieces of information into the image of the skin acquired by the electronic appliance so as to make said pieces of information recognizable by suitable image processing operations. By entering pieces of information is meant for example blackening, ticking or writing into areas delimited by markings on said medium. The meaning of areas is identified by suitable markings using alphanumerical characters which may be directly interpreted by the user. It is provided that, when there is insufficient room on the medium for directly writing the meaning thereof of the areas in proximity to the latter, the user refers to a map printed on a leaflet or on a screen in order to identify said areas as they appear upon examining the medium, by means of a caption which indicates their meaning. However there is no departure from the scope of the invention in the case of free markings which do not use areas dedicated to a particular meaning; the purpose of assigning dedicated areas to the meaning of the markings only has the goal of simplifying the image processing operations for extracting information. As regards skin analysis, this analysis may be improved by the knowledge of additional information such as the sex of the person, his/her ethnic group, his/her age, etc. Some of the additional information may be considered as sensitive information, in particular if they may be associated with identification items of the person such as a name, a telephone number, etc. These sensitive pieces of information may have a special status within the scope of the law of certain territories, in the invention, provision is made for the application of means such as cryptography and/or the use of trustworthy third parties for exchanging and/or storing the sensitive information in a secured way and only accessible to authorized entities.

The system according to the invention provides that the means for producing optical magnification of the image further comprise means for calibrating at least one characteristic of the image. Means are provided for including pieces of information with known characteristics in the same focusing plane than the surface of skin to be analyzed. Thus, the same image comprises the skin surface to be analyzed and known information in relation with the integrity of the image generally and/or with respect to characteristics of the image which are in relation with the characteristics of the skin which are to be analyzed. Thus, provision is made for correcting a certain number of optical aberrations such as geometrical and chromatic aberrations, vignetting, distortions. This allows the use in said image-sharpening means of low cost lenses made by molding or further so-called Fresnel lenses having relatively unrefined optical properties. In the invention, provision is also made for calibrating the image processing operations used for analyzing the skin. For example, color controls are provided for calibrating the recognition of the state of the reagents seen earlier and/or for calibrating the processing operations aiming at determining the color of the skin i.e. the colorimetric resultant due to dosages of melanin, carotene and hemoglobin specific to the skin sample to be analyzed. The inclusion of pieces of information for calibrating the color is particularly relevant in the alternative embodiments of the invention where the image-sharpening means do not have their own light source but use an external light source, the chromatic characteristics of which are unknown. Provision is also made for analyzing the radiance of the skin i.e. its brightness after calibrating image processing operations relative to a plurality of known brightness controls, the image of which is strictly acquired under the same conditions as that of the image of the skin surface to be analyzed. As regards the calibration of the geometrical characteristics of the image acquisition in order to correct them by image processing if necessary, the invention provides the marking of equidistant graduations having a known X and Y pitch in a half plane relatively to an axis of symmetry passing through the optical axis of the electronic appliance/device assembly and of said image-sharpening means, said half plane being advantageously dedicated to supporting pieces of reference information which are added to the image of the skin surface during the acquisition. By the effect of symmetry, the correction of any distortion seen in the image of the half plane comprising the reference information which is known, may be applied to the corresponding locations in the half plane of the image of the skin. This mainly applies for geometrical distortions, for alterations of color, it is provided that the corrections may be applied in all the points of the image. In order to correct the alterations of the light distribution detected in a few points of the half plane of reference information, provision is made for using the laws of optics for correcting the image as a whole. In order to measure the skin relief by image processing, the invention for example provides utilization of the measurement of the shadow cast by the crests under tilted illumination. Taking into account the considerable influence of the illumination angle upon image acquisition and accumulation of inaccuracies of all types, only a image-per-image calibration may give utilizable Z results. For this purpose, engraving of reliefs with known characteristics is provided in the area of the image which is dedicated to the pieces of calibration information. Regardless of the means for adding pieces of information into the image and regardless of the combination of said pieces of information and their purpose, provision is made for coding the reference thereof by means of a compact marking such as a 1D or 2D barcode, the decoding of which is carried out by image processing. The querying of a database from the recognized code returns the complete knowledge on the characteristics of said pieces of information which are present in the image so as to carry out suitable correction and/or calibration processing operations.

The system according to the invention provides that the means for producing optical magnification of the image further comprise means for illuminating the area of shooting. Means are provided for illuminating the skin surface and if necessary pieces of information are added into the field of the snapshot. In more economical alternatives, these are passive illumination means such as a reflective surface which sends back light rays from an artificial or natural external source towards the surface, the image of which is desirably acquired. Provision is also made in alternatives of said image-sharpening means which are designed for an electronic appliance version equipped with a flash, a hole at the suitable location so that the light of the flash of the device may illuminate the skin surface as well as the additional pieces of information if necessary. In more sophisticated alternative applications of the invention, it is provided that said image-sharpening means comprise a light source. It is provided that this light source emits white light by means of an incandescent bulb or advantageously one or more light-emitting diodes. Provision is also made for being able to illuminate the image acquisition area with monochromatic light in order to reveal particular aspects of the skin. Among the different wavelengths of interest, ultraviolet light having a wavelength of about 365 nanometers is particularly interesting in dermatology for revealing skin lesions and infections. In the field of cosmetics, with an ultraviolet light source, it is possible to reveal by fluorescence of porphyrins, clogged pores and other details of interest which do not appear in white light. Provision is also made for using one or more laser diodes emitting at a visible wavelength and an electromechanical scanning solution, for example with a MEMS micromirror in order to describe the totality of the image to be acquired from the laser beam with point-like projection. The advantage of such a more costly solution to be applied is the obtained contrast and the possibility of more accurate measurement of skin relief. Provision is also made for alternatives of the invention applying polarizing filters for improving the contrast and reducing the influence of parasitic reflections, which allow image capture of better quality which is favorable to better execution of the image processing operations according to the invention.

The system according to the invention provides that the means for producing optical magnification of the image further comprise means for determining the focusing distance by contact between a hardware element and a portion of the body of the person, of whom at least one characteristic of the skin is desirably analyzed. The system according to the invention is provided so as to be directly used by the general public. In order to make its use as simple as possible, provision has been made for suppressing any focusing adjustment. The different alternative means for producing optical magnification of the image are advantageously laid out so as to set all the distances having an influence on the focusing by contact between the relevant elements. In said first alternative, two distances have an influence on the focusing, the distance between the skin and the optical means and the distance between the optical means and the objective of the electronic appliance. Both of these distances are set by design as this will clearly appear in the detailed exemplary embodiments.

In said second alternative, the only distance having an influence on the focusing is the distance between the skin and the optical means.

In certain alternatives it is provided that a strut or rod integral with the means for producing optical magnification of the image is brought into contact with the skin in order to determine the optimum image acquisition distance. The end of the provided elements for coming into contact with the skin are advantageously laid out so as to avoid hurting persons notably upon acquisition of images in locations such as the contour of the eye, the eyelids, the corner of the mouth, the forehead, the neck.

The system according to the invention provides that the means for producing optical magnification of the image further comprises means for providing at least one piece of information to the user. It is provided that said at least one piece of information relates to instructions for mounting and/or using said means. In a particular advantageous way, it is provided that said at least one piece of information is in relation with the destination of the data produced by the consumer electronics device. This is for example the telephone number of a server capable of receiving MMSes, an electronic mail address capable of receiving image files as a email attachment, an address of an ftp server or website capable of allowing images to be loaded on a server, a physical mail address allowing the sending by mail of at least one print of images or a hardware medium containing data coding at least one image.

The system according to the invention provides that the means for producing optical magnification of the image are laid out so as to be delivered to the users in a form with small thickness using flexible materials so as to be able for example to be inserted in a magazine or sent in an envelope. Within the scope of a general public use of the invention in the field of cosmetics, it is particularly preferred to lay out said image-sharpening means so that their production and distribution costs are as low as possible, being aware that once said at least one characteristic of the skin of a given person is analyzed, said image-sharpening means are no longer useful. The fact that these means according to the invention, within this scope of use, are single-use means allows application of inexpensive production techniques. These inexpensive production techniques which further are suitable for low cost bulk distribution, are particularly compatible with the use of means for transforming the expression of at least one chemical characteristic of the skin so as to allow said at least one chemical characteristic of the skin to be appreciated by image processing as described earlier. These means using chemistry are generally placed on a planar support protected from air and humidity in a suitable protective package, the whole forming a solution with a small thickness and furthermore relatively flexible.

In still more preferred alternatives, said image-sharpening means are made by die-precutting in a sheet of a flexible material such as cardboard or an advantageously biodegradable or recyclable plastic material. The required optical means may be made in a rigid material taking into account their small surface area and their thickness which may remain compatible with insertion constraints and which does not affect the globally flexible nature of the proposed solution. Provision is also made for using optical means using lenses, so-called Fresnel lenses, for making flexible lenses with a very small thickness bearing in mind their optical properties. The alternatives for applying the invention aiming at flat distribution are intended for final assembling carried out by the user before proceeding with the analysis. Thus, the image-sharpening means will advantageously be laid out so as to simplify the final assembling. The assembling instructions using as much as possible drawings will advantageously be printed on the sheet which is at the basis of the making of said image-sharpening means. Solutions based on folding are provided for simplifying the assembling, the latter comprising the detachment of the form delivered flat from its support if necessary, its unfolding in order to reconstruct the image-sharpening means in their volume suitable for their use. A complementary step for locking said means in a deployed position may be necessary depending on the alternatives. This may for example be the insertion of at least one tab in a slot provided for this purpose or the application of an adhesive.

The invention also provides a method for analyzing at least one characteristic of the skin by means falling under optics and image processing. The method according to the invention comprises steps during which:
- at least one digital image is acquired comprising a skin surface by means of a consumer electronics device;
- data in connection with at least one acquired image are recovered in a format suitable for image processing operations;
- the recovered data are processed, which are in connection with the acquired image so as to produce at least one piece of information in connection with at least one characteristic of the skin;

The first step relates to the image acquisition strictly speaking. It is provided that the contents of this step vary depending on the application options of the invention and on the directives associated with the application which are indicated to the user. More particularly it is provided that the image acquisition step comprises several sub-steps for taking snapshots of specific skin areas. This step is performed by using an appliance equipped with an image sensor.

The second step aims at recovering the data in connection with said at least one acquired image, in a standard format supported by the electronic appliance which is suitable for image processing. This step is most often performed in the appliance having been used for the step for acquiring the image but it is provided that it may be performed in one or several other appliances such as a computer or a digital tablet.

The third step is that of the processing of the recovered data which are in relation with the acquired image so as to produce at least one piece of information of interest related to said at least one characteristic of the analyzed skin. According to application alternatives, this step may be entirely performed in at least one remote server or it may be partly performed in the electronic appliance before transmitting the data to said at least one remote server for finalizing the processing operations, if necessary for storing the data in relation with said at least one image and/or for accessing at least one database and/or for returning information to the user.

The method according to the invention further provides that at least one digital image comprising a skin surface acquired by means of a consumer electronics device contains the head of the person of whom at least one characteristic of the skin is desirably analyzed. The image of the human head is particularly rich in information. The pieces of information which the invention intends to extract from images of the head of persons are for example the ethnic type, the sex, the type of hair, the belonging to an age group. etc.

In the invention, image processing operations are provided for automatically extracting all or part of the information of interest with the purpose of informing a database and/or for refining or completing the analysis of at least one characteristic of the skin by resorting to information stored in at least one database, this from knowing at least one piece of information extracted from the image of the person's head.

The method according to the invention further comprises a step during which:
  means are placed in order to produce optical magnification of the image before its acquisition, between the objective of said consumer electronics device and the skin for which at least one characteristic is desirably analyzed.

The acquisition of the image of a portion of the body representing a relatively large skin surface area with view to a first level of analysis, is directly possible with consumer electronics devices. Apart from the acquisition already mentioned of the image of the person's head which is of great interest and which is possible with standard electronic appliances without any accessory, direct analysis of at least one characteristic of the skin requires image acquisition characteristics at least of the macrophotographic type.

Current consumer electronics devices equipped with a video camera or still camera function do not always provide the required characteristics, this is why the invention provides the use of image-sharpening means during an image acquisition at a shorter distance than the shortest distance possible for which said consumer electronics device was designed. A step using such means according to the invention is provided with the purposes of analyzing at least one characteristic thereof and/or for examining a mole or a lesion related to skin cancer.

The method according to the invention further comprises a step during which:
  at least one piece of information is entered in said at least one image of the skin as it will be acquired by means of a consumer electronics device.

This step aims at allowing the user to enter information in fields provided for this purpose comprised in the image to be acquired by means of an electronic appliance. Explicit pieces of information are intended to be entered such as the age or age group, the sex, the belonging to a group or to an ethnic sub-group referring back to characteristics of the skin which are statistically known such as for example for the <<red haired skin>> sub-group of the Caucasian ethnic group. The input of information is provided as a marking in at least one location corresponding to at least one selection in an identified assertion and/or as direct writing of information by using alphanumerical characters, for example, entering information for identifying and/or addressing the person, the skin of whom is analyzed or to whom the returned information should be transmitted if this is not the same person. The main benefit of this step is to include information of interest in each image in an inseparable way from the image of a skin surface strictly speaking. Suitable image processing operations are used for extracting the information thus introduced into the image so as to be able to use them in the information processing system associated with the application of the invention. In certain application alternatives, provision is made for not storing the images after having extracted information included by the user and after a complementary step for deleting at least the pixels corresponding to the pieces of information included by the user. These alternatives of the invention further intend to continue to relate information added by the user to an image, no longer in a raw form of pixels in this image but in a decoded form, structured in metadata associated with the image, this information being comprised in the file associated with the digital image.

The method according to the invention further comprises a step during which:
  said at least one image of the skin as acquired by means of an consumer electronics device and/or the data from the processing of said at least one image, are corrected depending on calibration information which is introduced into the image by the means for producing optical magnification of the image.

This step, if necessary, aims at correcting defects of the image which are for example due to the use of optical and/or mechanical low quality means for making said image-sharpening means at a lower cost and/or in a form which may be delivered flat. With this step, it is further possible to calibrate all or part of the characteristics of the data in connection with the acquired image so as to strongly reduce, or even remove the influence of heterogeneity of the acquisition solutions of digital images applied in consumer electronics devices, from their characteristics and their performances. In certain application alternatives of the invention, it is provided that this step comprise image processing operations aiming at normalizing the images before the processing operations for the analysis strictly speaking. By normalizing is for example meant, reframing, putting back to scale, carrying out at least one rotation, correcting the colors etc., so as to allow comparison of several acquisitions of images of a same skin surface of interest accomplished at different instants and possibly with different appliances. The normalization processing operations are, in certain cases of application, a step for preparing the images before executing processing operations with view to analyzing at least one characteristic of the skin, the preparation of the images improving the efficiency of the analysis processing operations.

The method according to the invention further comprises a step during which:
  the localization information of a skin reaction visible in an image, the knowledge of the corresponding location on a support for application of the substance having caused the skin reaction and the knowledge of the nature of the substance which was deposited at the corresponding location on the application support, are compared so as to produce at least one piece of information related to the nature of the substance having caused the skin reaction.

By skin reaction within the scope of the invention is meant any visible sign in an image which is circumscribed to a specific localization and which appears full of contrasts relatively to the skin surface, which makes up the background of the image. A skin reaction is visible to the naked eye and in the image acquired by an electronic appliance by a change in color and/or by a change in relief.

The method according to the invention further comprises a step during which:
 a list of at least one product to be avoided in that it contains a substance identified in the previous step and/or a list of recommended products because they do not contain a substance identified in the previous step are received from a server, said products being identified by their trade marks in use on a given territory so as to guide the user in his/her purchases.

Advantageously, the references of said products to be avoided or recommended products will be accessible through themes in relation with everyday life and/or grouped relative to how they may be purchased, for example grouping the products which may be found in a same department or in a same specialized point of sale. Provision is also made for changing the order of appearance of the products in the lists depending on gradings or classifications from feedback from the users or further depending on position purchases in the lists per brands or vendors.

The method according to the invention further comprises a step during which:
 a trade entity proposes to sell products belonging to the category of products recommended in the previous step.

The method according to the invention further comprises a step during which:
 at least one product is selected from the products proposed for sale in the previous step.

The method according to the invention further comprises a step during which:
 the preferences of the user are stored in memory through the choices which he/she made in the proposals which are made to him/her. Said preferences associated with the user in a database are possibly used for promotional purposes and/or for pushing information of interest and/or for sending samples of products which may be attractive after a test and/or for proposing other products which may be attractive according to said at least one product selected in the previous step.

The method according to the invention further comprises a step during which:
 a transaction related to transfer of ownership of said at least one finally selected product is validated.

The method according to the invention further comprises a step during which:
 At least one question is asked to the user.

This step aims at giving the required information to the system if necessary, for example that it is not possible or not desirable to obtain this information automatically by image processing. According to application alternatives, the invention provides that all the known means for interacting with the user may be used for this purpose, for example by exchanging SMS, emails, questions and answers on a website, via a dedicated application executed on a smartphone, on a digital tablet, on a television set connected to the Internet, in a Set Top Box (adaptor box) connected to a television set, etc.

The method according to the invention further comprises a step during which:
 at least one piece of information is transmitted to a remote server from a consumer electronics device connected to a network.

With this step, it is possible to transfer the file corresponding to said at least one raw image from the consumer electronics device to at least one remote server in which processing operations of the image are executed in order to analyze at least one characteristic of the skin. A system architecture of the <<cloud>> type is particularly suitable in order to be able to automatically adapt the remote processing means to demand or for deballasting an excessive processing load in a conventional client-server architecture. According to alternative embodiments, it is provided that all or part of the processing operations according to the invention are executed on at least one server according to whether the consumer electronics devices used are respectively unsuitable or suitable for locally executing some of the processing operations according to the invention.

The method according to the invention further comprises a step during which:
 at least one piece of information coming from at least one remote server is received.

This step aims at delivering to the user at least one portion of the expected results after applying the method according to the invention. The nature and the contents of said at least one piece of received information depends on the use of the method according to the invention and on the means used for receiving it. In the case of a use in the field of cosmetics, the user for example receives a proposal of products adapted to the characteristics of his/her skin and/or to the preferences which he/she was able to communicate to the information system. Generally the step for receiving at least one piece of information in the field of cosmetics is followed by steps for selecting products, making the order and for payment.

In the case of a use in the field of dermatology and more particularly for early detection of skin cancer, the user for example receives a piece of information indicating that no problem was detected or is invited to rapidly consult a dermatologist in the case of detection of an abnormality or in the case of doubt. Generally the step for receiving at least one piece of information in the field of dermatology is followed by steps for providing a list of dermatologists or hospitals comprising a dermatology department near the user who has been localized beforehand, and if necessary, by an automated step for making appointments with advantageously handling of priority depending on the urgency of the case.

Provision is made for using the method according to the invention in order to propose at least one product adapted to the skin and/or by extension to the hair of the person, of whom at least one characteristic of the skin has been analyzed. Indeed, the constantly increasing variety and the increasingly fine segmentation of the offer of cosmetic products depending on the characteristics of the skin, and by extension of the hair, makes it increasingly difficult for the user to select products which are suitable for him/her. Further, for professionals of cosmetics, of production at the points of sale, the multiplication of the references increases the complexity and the cost associated with logistics and marketing. The invention not only aims at simplifying the selection of cosmetic products within traditional ranges but it is intended that it gives the possibility of multiplying without any limit the number of combinations between active substances and cosmetic bases. Provision is also made for coupling the invention with ordering and a distance selling system as well as with a suitable production management system, allowing quasi tailored manufacturing of cosmetic products, and possibly after their ordering.

The method according to the invention further comprises a step during which:

at least one product is selected in a set of at least one cosmetic product proposed as being adapted to at least one characteristic of the skin which was analyzed or related with the latter.

By assertion in relation with said at least one characteristic of the analyzed skin is meant the existence of at least one indirect relationship such as for example the proposal of products for treating frizzy hair after having detected a skin of the African type by applying the invention.

The method according to the invention further comprises a step during which:

the preferences of the user are stored in memory through the selections which he/she makes in the proposals which are made to him/her. Said preferences associated with the user in a database are possibly used for promotional purposes and/or for pushing information of interest and/or for sending samples of products which may be attractive after a test and/or for proposing other products which may be attractive according to said at least one product selected in the previous step.

The method according to the invention further comprises a step during which:

a transaction in relation with the transfer of ownership of said at least one finally selected product is validated.

Advantageously it is provided that the selection step or the transaction step strictly speaking and/or the step of its validation is proposed to the user by means of the consumer electronics device used for analyzing the skin. For example, this step may be applied by using a simple mobile telephone which connects to a suitable voice server or to a person. This step may also be applied by using a simple telephone from which SMS or MMS are exchanged. A smartphone or a communicating tablet provided with a camera further offers the possibility of applying this step by means of a downloadable dedicated application. This being the case, there is no departure from the scope of the invention if another means is used for these steps, for example access to a vendor site by means of a generic web browser or by a specific application executed on a microcomputer, on a tablet or on a television set connected to Internet.

The method according to the invention further comprises a step during which:

a customer account is credited according to terms and associated benefits described in one or more public information media.

The method according to the invention further comprises a step during which:

the manufacturing of said at least one selected product is launched.

The advantages of the invention in this context are multiple, in addition to the proposal of products perfectly matched with the characteristics of the skin, and this easily for the user, and then the selection and acquisition of at least one product among the proposed ones, the launching of production after these steps further allows reduction and suppression of preservatives in the composition of the products. The suppression of long storage times in the production and distribution circuits makes preservatives less necessary or unnecessary. Moreover, the economic gains which result from the suppression of the long storage times allowed by the invention, are significant.

Provision is made for using the method according to the invention for detecting skin cancer in a person for whom at least one characteristic of the skin has been analyzed. Early detection of skin cancer increases chances of curing it. Indeed, it is known that skin cancer may have a good curing prognosis if it is treated in due time and if this is a dangerous type of cancer in that it is likely to develop rapidly and may in certain cases reach the metastatic stage in a few months. The invention is particularly relevant for early detection of skin cancer in that it notably gives the possibility to persons which are aware that they are at risk such as persons with red haired skin or those having had strong sunstrokes during their childhood, of monitoring themselves as often as desired, in a free economical and efficient way. Further, the invention gives the possibility of coping with the dual problem of constant progression of the number of melanomas which appear in the populations, with for example a progression from 5 to 7% in the number of melanomas diagnosed per year in Europe, and the relative shortage of dermatologists. With the invention, it is also possible to improve the frequency and therefore the timeliness of the detection of the melanoma without saturating the consultation capacities but on the contrary by orienting doubtful cases and proved detections to specialists for rapid and efficient management both for the patient and for the physician.

Provision is made for optimizing the data processing operations according to the invention applied to the image of a mole or a suspect skin lesion, in order to detect lesions which are:

of black color,
asymmetrical,
with irregular edges,
with non-homogeneous coloration,
of large diameter (>6 mm),
developing.

For this last category, it is provided that the system according to the invention integrates means for storing in memory a plurality of time-stamped images of the lesion which is being monitored. As the images are acquired at regular intervals within the scope of good prevention, it is provided that the system according to the invention automatically solicits any user already registered, by automatically sending an electronic message, with reminders if necessary, when it would be desirable to carry out a fresh acquisition because of a too long time having elapsed since the last acquisition. Image processing operations are further provided for readjusting the unit images, for example in rotation, in translation in the plane of the image, changing the scale, in order to allow automatic comparison thereof.

Provision is also made for using the method according to the invention in order to detect the sensitivity of a person to one or more allergenic substances. It is commonly seen that the number of allergenic substances continues to increase as well as the sensitivity of persons. In addition to the discomfort for the relevant persons which should be reduced at least in order to allow them to be aware of the substances to which they should avoid exposure, allergies are becoming a public health issue taking into account the importance of the phenomenon. Searching for the cause of an allergy with means of the state of the art may be long and tedious. With the invention it is possible to facilitate and accelerate the obtaining of results upon searching for the cause of an allergy. The solutions of the invention further allow the general public to themselves proceed with this search and at least with a preliminary search aiming at narrowing the field of the search which will be finalized by an allergologist. The information in relation with at least one characteristic of the skin is binary in this application. It is based on the detection of the presence or the absence of a visible skin reaction by a change in color and/or a change in skin relief localized at the location which was in contact with the allergenic substance. This information is utilized in a complementary comparison step between the localization of the skin reaction in the image, knowing the corresponding location on the support of application of the allergenic substance and knowing the nature of the substance which was deposited at this location on the support.

The invention used for seeking allergenic substances is based on the use of specific consumables which are different from those described earlier within the scope of applications to cosmetics and to detection of skin cancer. The consumable according to the invention for seeking allergenic substances comprises a support on the surface of which is deposited a plurality of possibly allergenic substances. The deposits of substances are advantageously organized as a matrix within a regular grid materialized by visible means. A grid which appears full of contrasts in the image allows the making of consumables having a large density without any risk of a reading error. For this purpose, it is advantageous to materialize a framing of one or more substance deposition sites both by a dark color marking and a light color marking so that regardless of the color of the skin of the person, there are always visible marks in the image with respect to the background color of the skin. The surface supporting the plurality of allergenic substances advantageously comprises as many means for causing a microlesion of the skin as there are substances, so as to put said substances in contact with the tissues placed under the skin barrier and which are accessible to the immune system during the step for applying the consumable according to the invention on a skin surface. The means for causing microlesions are preferably laid out so that the application remains painless. The preferred embodiment is a substrate consisting of a plate of flexible plastic material with a small thickness, one face of which is structured in order to form on each site intended to receive a possibly allergenic product, one or more microtips or microstrips laid out so that moderate pressure exerted with fingers or via an accessory provided for this purpose on the other face causes the required microlesions for putting into contact each substance, the effect of which is to be tested and the immune system. It is further provided that the consumable according to the invention may be partly removed after a sufficient exposure period of the immune system to the substances to be tested for the image acquisition step according to the invention. The minimum portion of the consumable to be removed for this step is that which conceals the points where the immune system has been exposed to the substances. The maximum portion of the consumable to be removed for this step is that which during the image acquisition step visibly leaves:

- sufficient elements of the structure according to which the points contacting the substances were organized in order to be able to determine by image processing and/or by calculation the position of each contact point, and
- means for identifying the consumable so as to allow the image processing operations to request in the database the whole of its characteristics required for analysis.

After the image acquisition step, the residual elements of the consumable may be removed from the skin. The image processing analysis according to the invention is based on the detection of the points having caused a reaction of the immune system and on the identification of one or more substances having caused the reaction by their localization in the image and by the matching between the localization of the points in the image and the substances put into contact while being aware of the characteristics of the consumable with regard to the nature of the substances which it comprises and to their respective localizations.

BRIEF DESCRIPTION OF THE DRAWINGS

Other advantages and characteristics of the invention will become apparent upon examining the detailed description of embodiments which are by no means limiting and the appended drawings wherein, according to the first aspect of the invention.

DETAILED DESCRIPTION OF FIGURES AND OF PREFERRED EMBODIMENTS

Figure 1:
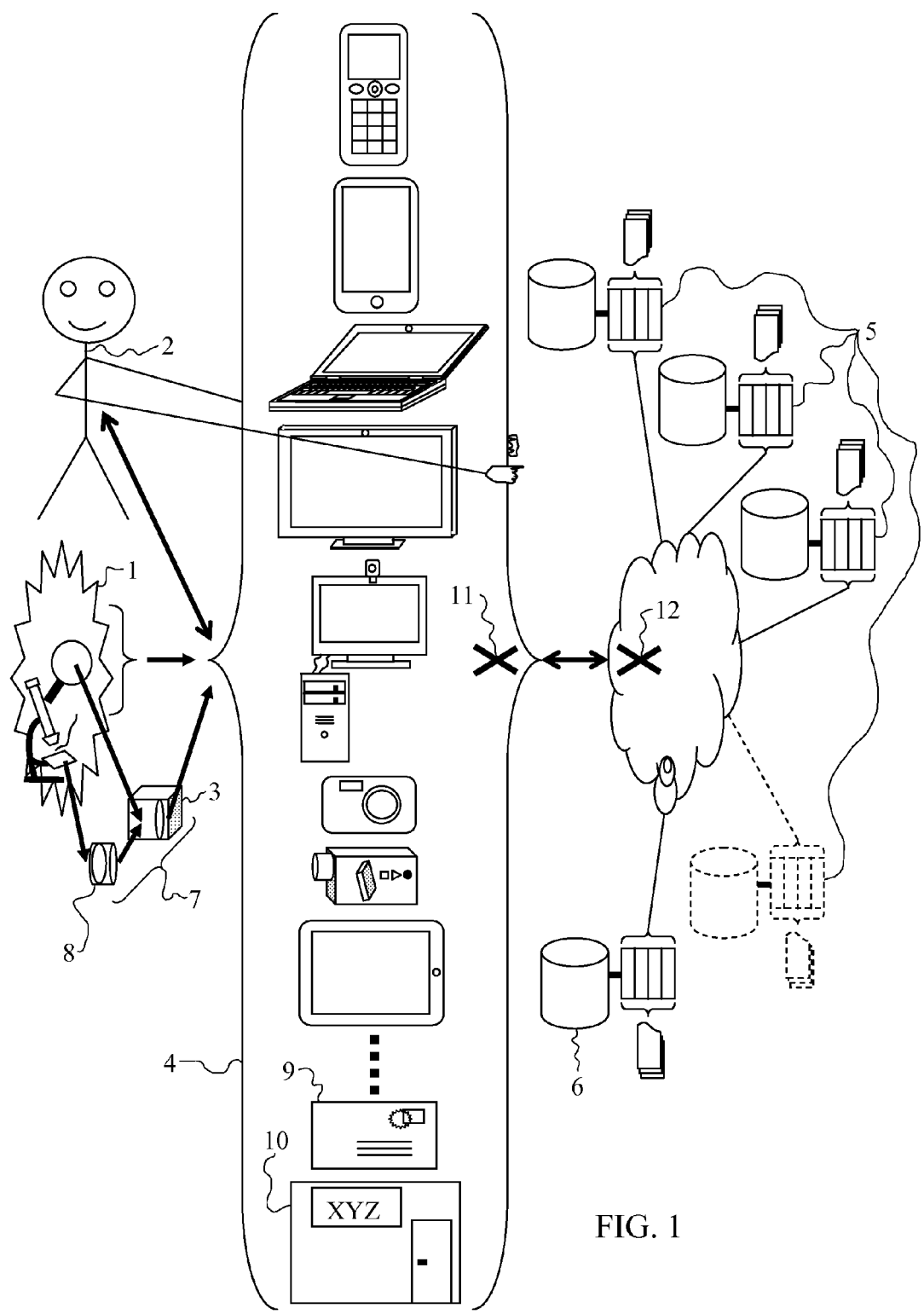
FIG. 1 illustrates the global architecture of the system according to the invention.

Other particularities and advantages of the invention will further become apparent in the description hereafter. In the appended drawings given as non-limiting examples:

FIG. 1 illustrates the global architecture of the system according to the invention.

At least one characteristic of the skin 1 of a person, which may be the actual user 2 or a third party person, is to be analyzed by means mainly falling under optics (3, 4) and under image processing (4, 5). It is provided that other techniques complete these means notably for accommodating imperfections of consumer electronics device 4 used and/or limitation of knowledge in the field of the skin of the general population which is mainly targeted by the invention. The provided complementary techniques are for example the answer to explicit questions and/or the resort to statistical models and/or to querying databases 6 in relation with genetics.

According to the characteristics of the skin which are desirably analyzed, being aware that from a few analyzed characteristics, other ones may be inferred by resorting to the aforementioned complementary techniques, the invention provides the use of one or more consumer electronics devices 4 in order to acquire one or more images and to transmit the corresponding data to processing means (4, 5). The invention further provides that the acquisition of an image of a skin surface is accomplished directly from an consumer electronics device 4 and/or by using means 7 for producing optical magnification of the image. These means if necessary comprise several sub-sets (3, 8) for obtaining the magnification in particular required for analyzing hair.

The invention further intends to extend the notion of consumer electronics means to all the means accessible to the general public, for example automatons for producing passport photographs. As regards the transmission of the produced information to remote processing means, in addition to the use of the preferred means falling under telecommunications and of the connection of consumer electronics devices to networks, provision is also made for the use of networks for transporting information over physical media such as mail 9 or provision of information in determined physical locations 10 depending on the field of use of the invention. Such locations are for example beauty centers in the field of cosmetics or medical practices in the field of dermatology.

According to alternative embodiments of the invention it is provided that the produced information to be transmitted to remote means is raw information directly stemming from the image acquisition step, information partly or totally processed by means falling under consumer electronics which are available to the user.

Of course, the means which may be used for transmitting information in the direction from the user to the outer information processing systems, may also be used for transmitting information and/or goods and/or services to the user from remote entities. It is further provided that the means accessible to the general public used for producing information are different from those used for receiving it, this is what symbolizes the cross 11. Provision is also made for using a plurality of interconnected networks in order to transmit information between the applied means, this is what symbolizes the cross 12. For example, the user 2 may acquire an image of the skin 1 with his/her mobile telephone, send the corresponding file via MMS or as an attached document to an email via the cell telephone network, the information is received by a server via an IP network interconnected with the cell phone network. Moreover, transmissions of data via interconnected networks are also provided on the server side. It is provided that a plurality of interconnected servers share the computing power and the storage means within the scope of a distributed architecture of the <<cloud computing>> type. It is also provided that the servers 5 transmit requests to also interconnected remote databases 6. The return information and/or the goods and/or the services associated with the skin analysis according to the invention are made available to the user through at least one means accessible to the general public 4, these means being mainly electronic means connected to a network but also possibly forwarding means or means for making them physically available.

Figure 2:
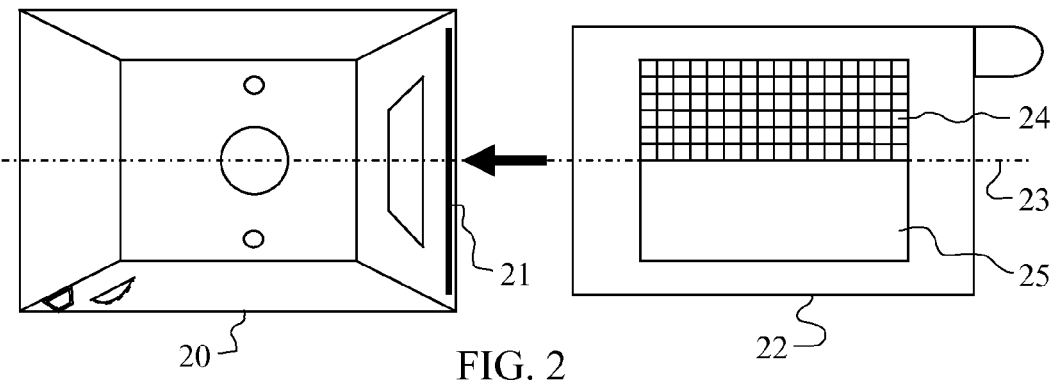
FIG. 2 illustrates a first alternative of magnification means.

FIG. 2 illustrates a first alternative of means for producing optical magnification of the image. This first alternative gives an example of application of said image-sharpening means according to the invention in the form of a qualitative and durable object capable of being used by the general public but also by professionals. The technical solutions used in this non-limiting example are a rigid casing 20 in injected plastic material in which are placed an electronic sub-assembly and optical means for sharpening the image at a shorter distance than the shortest distance for which the consumer electronics device used for acquiring the image has been designed. A convex glass or plastic material lens of optical quality is used for this purpose. An assembly of lenses is also provided for very qualitative alternatives wherein it is sought to reduce optical distortions and aberrations at the source in order to for example reduce the needs for image processing operations and for reducing the response times of the system. Means 21 are provided for introducing and for guiding a sub-assembly 22 placed in the plane of the image of the skin to be acquired. Said sub-assembly is laid out so as to transform the expression of at least one physical, chemical or biological characteristic of the skin so as to allow appreciation of said at least one physical, chemical or biological characteristic of the skin by image processing and/or means for allowing the user to enter at least one piece of information into the image and/or for calibrating at least one characteristic of the image. Said sub-assembly utilizes the symmetry of the optical means but also advantageously the symmetry in the distribution of light on the surface for which the image is desirably acquired. In the example of FIG. 2, a symmetry exists on either side of the axis 23 for the optical means and for the illumination means. Thus in the example of FIG. 2, the response of the complete system, during acquisition of the image comprised in the half plane 24 for each point is equivalent to the response for the symmetrical point in the half plane 25. The correction and/or calibration processing operations according to the invention are based on the knowledge of the characteristics of the image of a reference half plane 24 and on the correction of the characteristics of pixels, of blocks of pixels, of the reference half plane of the image acquired for obtaining the result known beforehand. Next, the same corrections are applied to the symmetrical pixels or symmetrical blocks of pixels of the half plane 25 of the acquired image.

Figure 3:
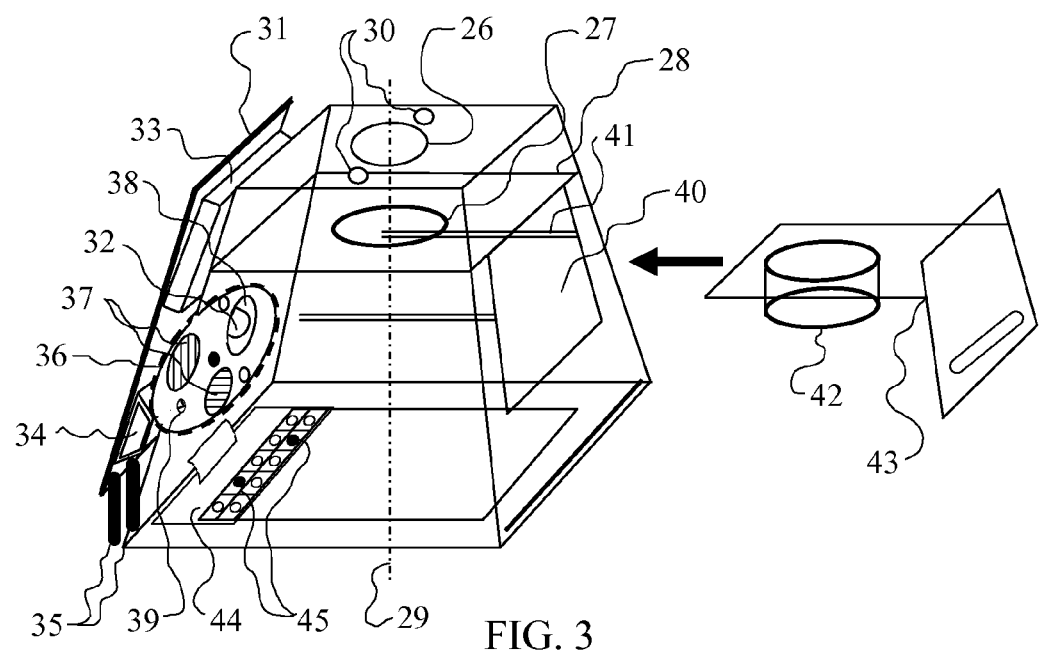
FIG. 3 illustrates the internal architecture of the means of FIG. 2.

FIG. 3 illustrates the internal architecture of the device of FIG. 2. This figure shows in perspective and in transparence the main elements of the device. The objective hole 26 to be placed facing the objective of the consumer electronics device; the optical means, such as at least one convergent lens 27, on their support 28 in order to mechanically attach them in the alignment of the optical axis 29 passing through the center of the objective hole and the center of the plane of the image to be acquired at the suitable distance from the objective of the consumer electronics device and from the plane of the image to be acquired. Holes 30 are provided in order to attach for example with screws or rivets, an intermediate part for adaptation to a given electronic appliance version or an intermediate part provided with adjustment means capable of allowing adaptation to a plurality of consumer electronics device versions. Alternatives of the device are also provided which are directly compatible with very widespread electronic appliance models without having to resort to an intermediate adaptation part. The electronic sub-assembly 31 is provided for comprising the light source 32, its self-contained electric power supply means, for example a polymeric Li-Ion accumulator 33 rechargeable through a USB connection 34 to a computer or a charger like for most of the consumer electronics devices such as personal media players, mobile telephones or tablets. In this advanced application alternative, two electrodes 35 trigger the switching on of the light source when they come into contact with the skin. The contact with a table or any support made in an insulating material not causing switching on of the light source. A timeout, which automatically switches off the light source when it expires, is re-initialized as long as the probes are in contact with the skin. In this example, a filter holder wheel 36 gives the possibility of easily selecting the type of light by rotating the thumbwheel, which brings the filter of interest 37 in front of the light source, for example a polarizing filter laid out for allowing measurement of skin relief, a polarizing filter laid out for improving the contrast of the image, a filter mainly letting through ultra-violet light from a source producing white light by excitation of phosphors. In certain alternative embodiments, a position is provided partly occulting the light source, for example only letting out the light in a low portion or through a slot, so as to improve appreciation of the skin relief by producing light consisting of parallel rays. One position 38 is provided for entirely letting through the light of the source and an indexing mechanism 39 allows accurate positioning of each filter in front of the source. This application example further comprises an aperture and guiding means 41 for receiving complementary optical means 42 for providing high optical magnification of the image, on their support 43. In particularly elaborated alternatives of the device according to the invention particularly aimed at uses in the field of cosmetics, indirect electronic means are provided for transforming the expression of at least one physical, chemical or biological characteristic of the skin so that said at least one physical, chemical or biological characteristic of the skin may be appreciated by image processing. This technical solution is particularly of interest within the scope of devices according to the invention which may be used by professionals since the sensors do not resort to consumable solutions and the accuracy of the analysis is greater than those which may be provided by solutions based on reagents which change color. This latter solution is preferred when low cost of the device is the main criterion for selecting the applied technical solutions. In the non-limiting example of FIG. 3, the addition of transformation functions to the basic functions already described, comprises the addition of a humidity sensor capable of providing a measurement which may be linearized over a wide range. The humidity sensor is laid out so as to come into contact with the skin in order to measure the surface humidity thereof when the device as a whole is placed in a functional position. In certain alternatives provision is made for removing the simple electrodes 35 provided for an on/off operation within the scope of automatic handling of the light source, by a program component executed by a microcontroller. This program is based on detecting the crossing of a threshold by the result of the measurement of the surface humidity in order to automatically drive the light source. Thus the light source is automatically enabled when the surface humidity is greater than or equal to the minimum value for human skin. The light source is disabled when the value is less than the threshold during a time determined beforehand, which corresponds to the laying on a non-organic surface when the device is not used. Further provision is made for adding means for evaluating the elasticity of the skin. Means based on the damping of vibratory pulses, on the displacement of a resonance frequency, on the propagation of a vibratory wave using the skin as a propagation medium are particularly suitable technical solutions. The means 44 are laid out so as to place display means in the field for acquiring the image. Any static display means, i.e. non-multiplexed, based on emissive technologies such as light-emitting diodes, LEDs or OLEDs, may be used as well as solutions based on controlling the reflection of light or its transmission such as micromirrors, LCDs or further electronic ink. In the example of FIG. 3, traditional LEDs are used for including the information in the image. Very little energy is required for the active LEDs 45 to be visible when they are oriented towards the image acquisition means. Advantageously, the LEDs are centered in elementary areas materialized by black lines and arranged in lines or columns for a given variable to be transmitted. By coding the measured value, for example in binary, it is possible to limit the number of LEDs. For example, 7 LEDs allow coding of all integer values ranging from 0 to 100. Five LEDs on one scale where a single LED is lit at a time nevertheless allow a variable to be coded on a scale from 0 to 100 with steps of 20. The LEDs organized as 7-segment displays are also an option provided in certain alternatives.

Figure 4:
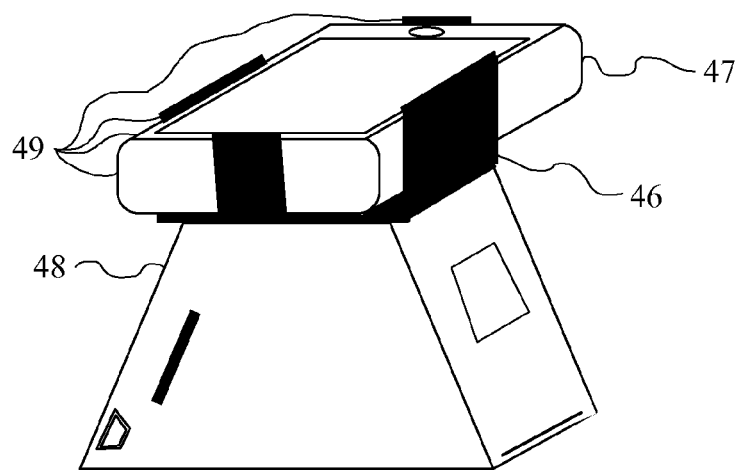
FIG. 4 illustrates the means for attaching the example of FIG. 2.

FIG. 4 illustrates the means for attachment of the example of FIG. 2. This figure illustrates the case of the use of an adaptation part 46 intended for a given model of an consumer electronics device 47. In this alternative, the adaptation part is designed for an iPhone from Apple Computers (registered trademarks) for attaching the device according to the invention (46, 48) with clips clamping the electronic appliance 47 over its width and over its length. Thus, both objects form an integral assembly and the optical axis of the device 48 is found exactly aligned with that of the objective of the electronic appliance 47 without it being necessary to be concerned about this. The clips are in an elastic plastic material or in a flexible metal advantageously coated with a material which ensures protection of the surface of the appliance which is in contact with it.

Figure 5:
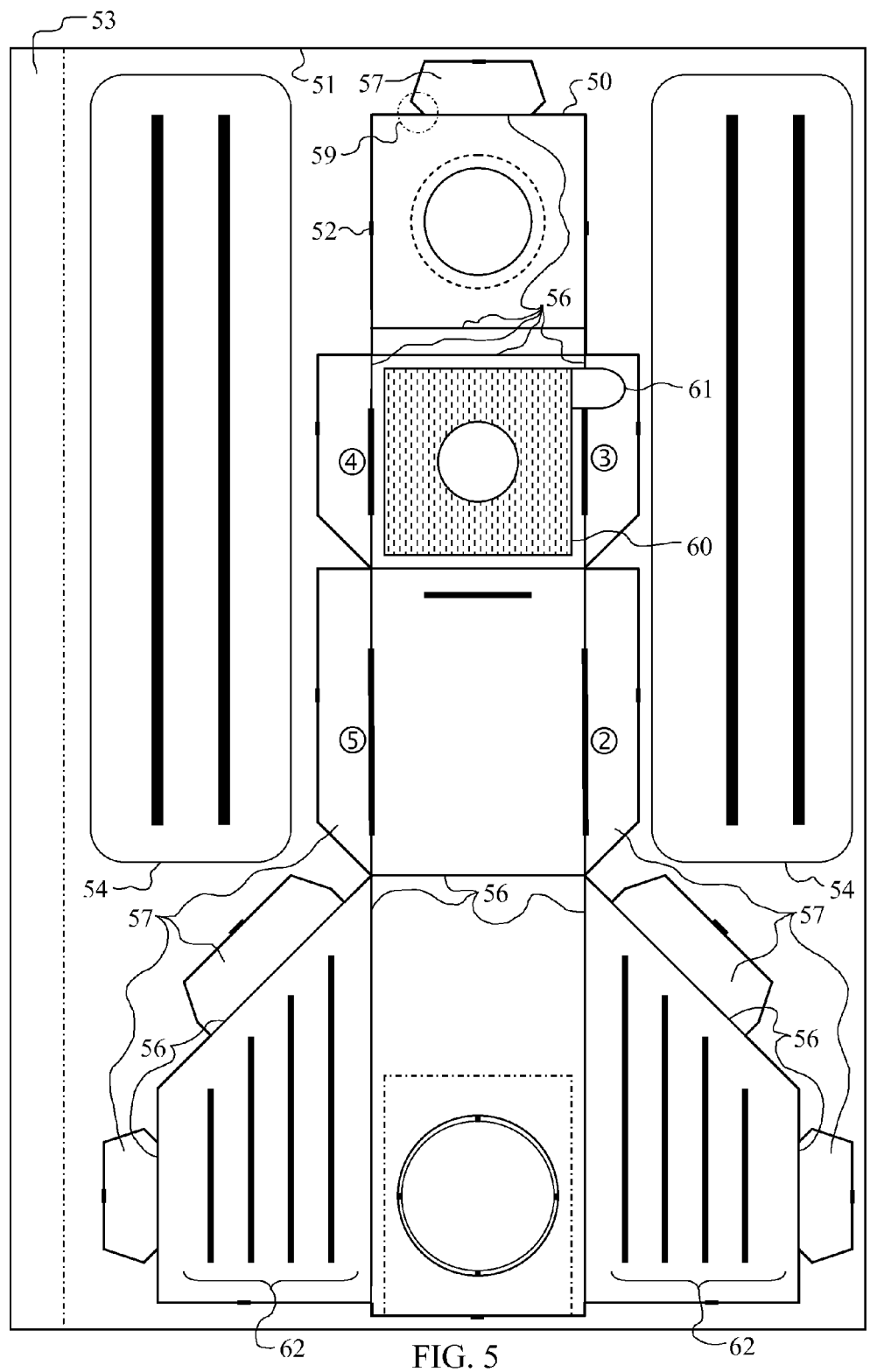
FIG. 5 illustrates a first flat deliverable alternative, external face.

FIG. 5 illustrates a flat deliverable sub-alternative of a first alternative means for producing optical magnification of the image. This is the preferred alternative embodiment within the scope of an application of the invention in the field of cosmetics. This version of the device for producing optical magnification of the image may be inserted into a magazine or may be forwarded to its addressee in a simple envelope by postal services. This sub-alternative is further not very costly to make, which makes it particularly suitable for promotional operations or massive marketing campaigns. The making only requires conventional operations for cutting out with a die, for sizing and laying the lens and a protective film on the adhesive surface. All the steps of the method for making the sub-alternative are further easily automatable and only require ordinary machines capable of producing large amounts of devices. The final mounting of the device is ensured by the user. The invention intends to facilitate the mounting of the device by its actual design. Thus, the example of FIG. 5 provides the precutting of the flat shape of the device 50 in a cardboard or plastic material sheet 51, advantageously selected for its capability of being recycled or biodegraded. The precutting of the flat shape of the device provides a few non-cut ties 52 distributed over its perimeter in order to make it integral with the sheet 51 in which it is included until it is made available to the user. In the case of an insertion of the device in a magazine, a margin 53 is provided on the side of the binding. FIG. 5 illustrates the external face of the device delivered flat. The surfaces 54 of the sheet 51 which do not comprise elements of the device, are advantageously used for receiving imprints falling under communications for promotional purposes in connection with the brand associated with the distribution operation of the device in a commercial context or in connection with the organization upon the initiative of a distribution of the device in a skin cancer screening context. In this example, the assembly of the flat shape 50, after having been detached from its support 51 rests on folds along folding lines 56 which are advantageously materialized by thinning of the material along an orientation facilitating folding in the suitable direction with the purpose of making the assembling more intuitive. Maintaining the reconstructed volume after folding is based on tabs 57 to be introduced into slots 58. All or part of said tabs are laid out so as to remain blocked once they are inserted into the corresponding slots, by their shape 59 or by using solutions based on adhesives. The face of the device which is provided for coming into contact with the consumer electronics device is coated with a so-called repositionable adhesive, i.e. which in addition to the fact of being easily detached and stuck again several times, guarantees observance of the integrity of the surface of the consumer electronics device in contact of which it is found. Markings are also provided on one or on several of the visible portions of the device once it is assembled for providing at least one piece of information to the user. FIG. 5 illustrates the marking of information in connection with the destination of the data produced by the consumer electronics device. These pieces of information 62 for example are the telephone number of a server capable of receiving MMSes, an electronic mail address capable of receiving image files as an attached enclosure and an address of a website capable of allowing the loading of files of digital images into the bulk memory of a remote server.

Figure 6:
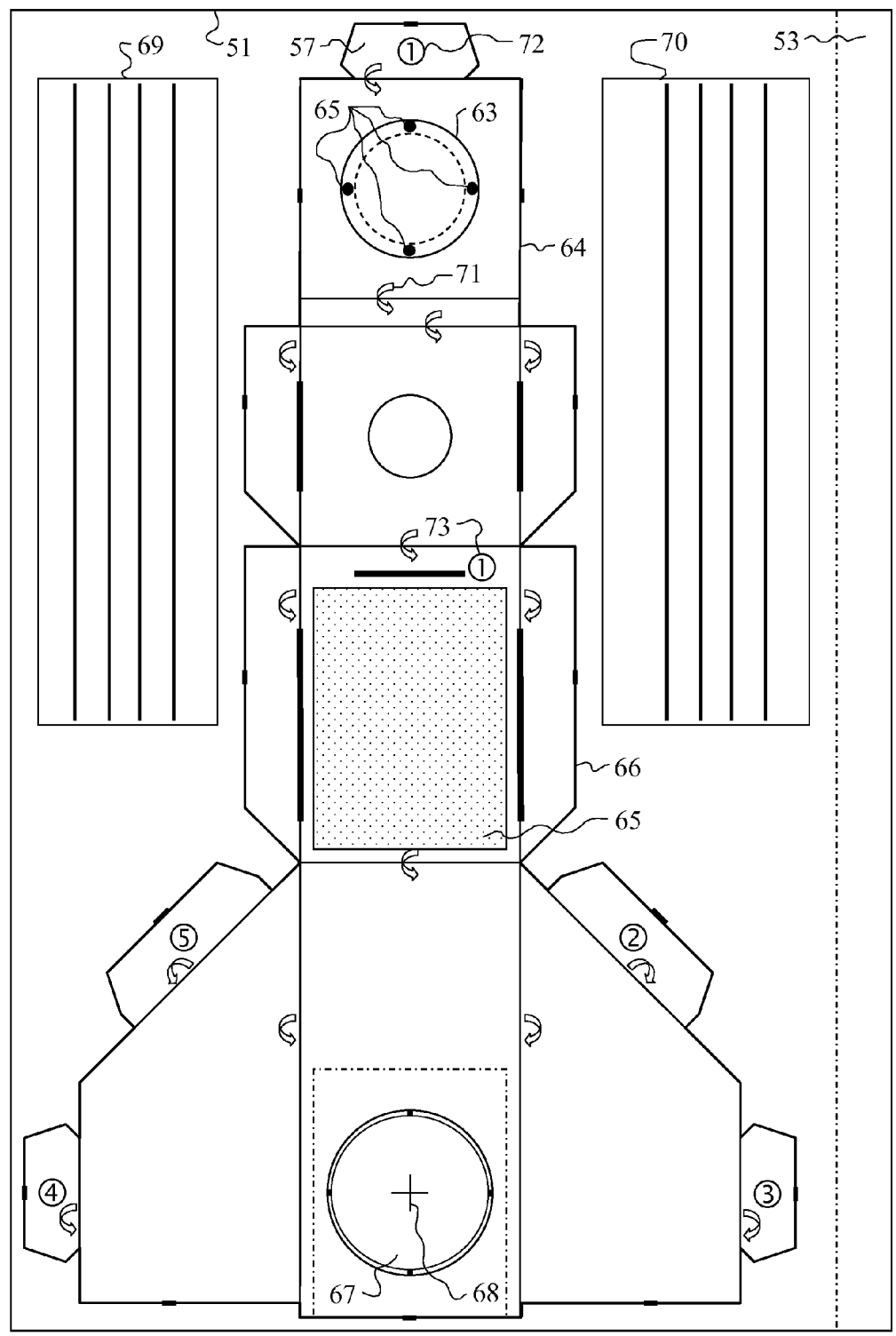
FIG. 6 illustrates the internal face of the flat alternative of FIG. 5.

FIG. 6 illustrates the internal face of the flat alternative of FIG. 5.

In this exemplary embodiment of the invention, it is towards the interior that the different faces and tabs are folded. It is provided that the folding lines be marked by the tooling during the precutting in order to facilitate folding in the suitable direction. The orientated pre-folds are made by means of part of the tooling, the V-shaped section of which applies sufficiently strong pressure on the folding line in order to form the folding line but without going as far as cutting the material. The internal face further receives a conversion lens 63 which is attached in alignment on the optical axis on an intermediate stage 64 of the device. This intermediate plane is located, after final assembly of the device, between the plane which is in contact with the electronic appliance and the one which is in contact with the skin. The attachment of the lens is for example achieved by spots of adhesives affixed on said intermediate plane before laying the lens so that the peripheral area of the lens receiving the adhesive is not placed in the field of the image. A reflective coating 65, for example an aluminized film is affixed on the tilted plane 66 in order to send back light arriving through the aperture of the device into the plane of the image to be acquired. In certain alternative embodiments, the reflective coating is removable and may be concealed by a complementary removable flap so as to illuminate the plane of the image with light having rays tilted according to a suitable angle in order to measure the skin relief under optimum illumination conditions. In order to facilitate the alignment of the objective of the electronic appliance on the optical axis of the device, it is intended to utilize the surface of material 67 obturating the portion of the plane of the image to be acquired corresponding to the skin surface and if necessary to the calibration information. A cross 68 or any other remarkable graphic element is printed at the intersection of the plane of the image and of the optical axis of the device and the user is required to center this element in the image as it appears on a control screen of an electronic appliance. When the cross actually appears at the center of the image acquired by the electronic appliance then the latter is laid on the adhesive surface of the device in order to firmly attach both objects without misaligning the optical axis or modifying the relative orientation of the appliance with respect to the device. Provision is made for facilitating the final assembly of the device by using a face of the support 51 for receiving imprints in relation with the assembly instructions 69 and to the instructions for use 70 of the device. These instructions may advantageously be made in the form of cartoons capable of being understood in all languages. Provision is further made for means for guiding the user in the final assembly by imprints on the elements of the actual device, for example, arrows 71 indicating in which directions the folds are made, numbers 72 on the tabs 57 which should correspond with those of the slot 73 into which they have to be inserted.

Figure 7:
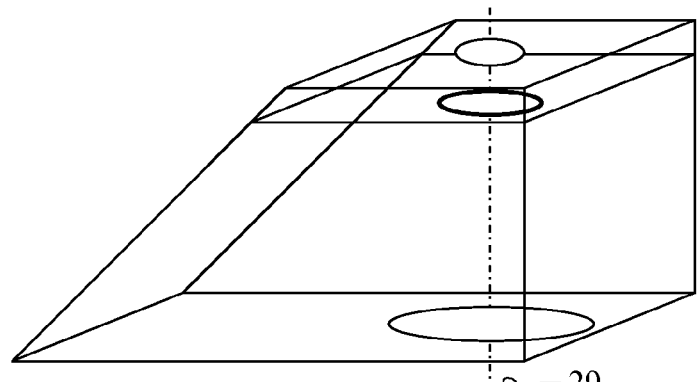
FIG. 7 illustrates the flat alternative of FIG. 5 in volume.

FIG. 7 illustrates the flat alternative of FIG. 5 in a volume presentation.

The device delivered flat gives the bulk object of FIG. 7 when it is assembled. The center of the hole of the face comes into contact with the electronic appliance, the center of the lens and the center of the face come into contact with the skin surface and are aligned on the optical axis 29.

Figure 8:
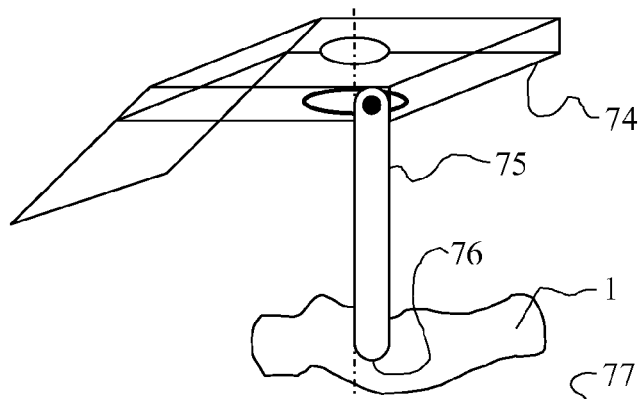
FIG. 8 illustrates a sub-alternative of the alternative of FIG. 5.

FIG. 8 illustrates a sub-alternative of the alternative of FIG. 5.

This sub-alternative again repeats the general principle of the device of FIG. 6 but in the form of two detachable sub-assemblies. This sub-alternative has the advantage of allowing acquisition of non-planar skin surface images such as in the region of the contour of the eyes, of the corner of the lips, of the neck etc. The first sub-assembly 74 comprises essential means for acquiring an image and means for maintaining the assembly formed by the electronic appliance and said first sub-assembly of the device according to the invention at a distance from the skin surface which is suitable so that the image is sharp. The means for maintaining the proper distance so that the image is sharp assume the shape of a strut 75 in the example of FIG. 8. The distance determining the sharpness of the image is set by putting the end of the strut 76, in the deployed position if the strut is retractable, in contact with the skin 1. The end of the strut 76 is laid out by its shape and/or by its material so as not to risk injuring the person. The optics of this sub-alternative is further laid out so as to give preference to the field depth over the magnification so as to retain a sharp image in spite of a significant change in the distance of the different points on the non-planar surfaces of interest. Versions are provided which only comprise said first sub-assembly 74 of the device as shown in FIG. 8. In these compact versions, the supporting strut(s) on the skin are advantageously retractable as well as, if necessary, at least part of the reflective surface or the on-board illumination means. Other versions comprise both sub-assemblies (74, 77), the device may then be used as described in the examples of FIG. 2 or 5 when both sub-assemblies are assembled. These versions further provide the possibility of detaching both sub-assemblies (74, 77) and of only using the first sub-assembly 74 with the purposes of acquiring one or more images of skin surfaces at locations which are not planar, or the surface of which is not sufficient for being able to place the base of the second sub-assembly 77, or for which the field depth is insufficient so that the image is sharp when the base of the second sub-assembly 77 bears upon protruding body portions. It should be noted that the reflective portion integral with the first sub-assembly may be a reduced or nil surface with respect to the surface which is required for suitably illuminating the skin surface in a configuration where two sub-assemblies are assembled. Indeed, used alone, said first portion is sufficiently openworked so that sufficient light reaches the skin surface, the image of which is intended to be acquired.

Figure 9:
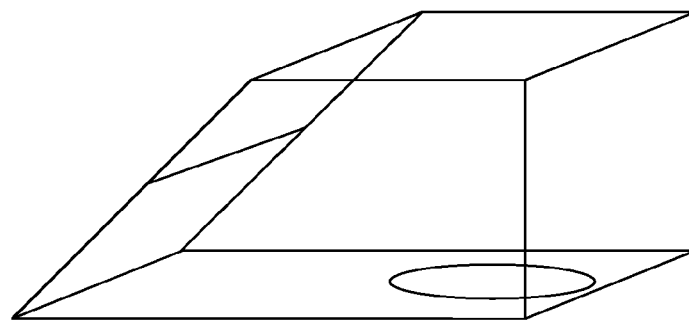
FIG. 9 illustrates the flat alternative of FIG. 5 in an operational situation.

FIG. 9 illustrates the flat alternative of FIG. 6 in a real-life situation.

The device of FIG. 6 in perspective and in a functional situation, is attached to a consumer electronics device 47 and in contact with a skin surface 1. The height H of the device determines by design the distance between the objective of the electronic appliance 47 and the skin surface 1 in order to have a sharp image. An aperture 78 to be rotated towards an external source of natural or artificial light illuminates the plane of the image to be acquired.

Figure 10:
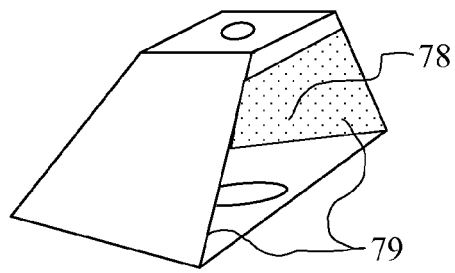
FIG. 10 illustrates another sub-alternative of the alternative of FIG. 5.

FIG. 10 illustrates a sub-alternative of the flat alternative of FIG. 5.

This sub-alternative is laid out so as to allow more incoming light than in the version of FIG. 5 with an aperture 78 of larger surface area. The side walls 79, which are covered with a reflective coating such as the reflective face opposite to the aperture, are further used for contributing to illuminating the plane of the image to be acquired.

Figure 11:
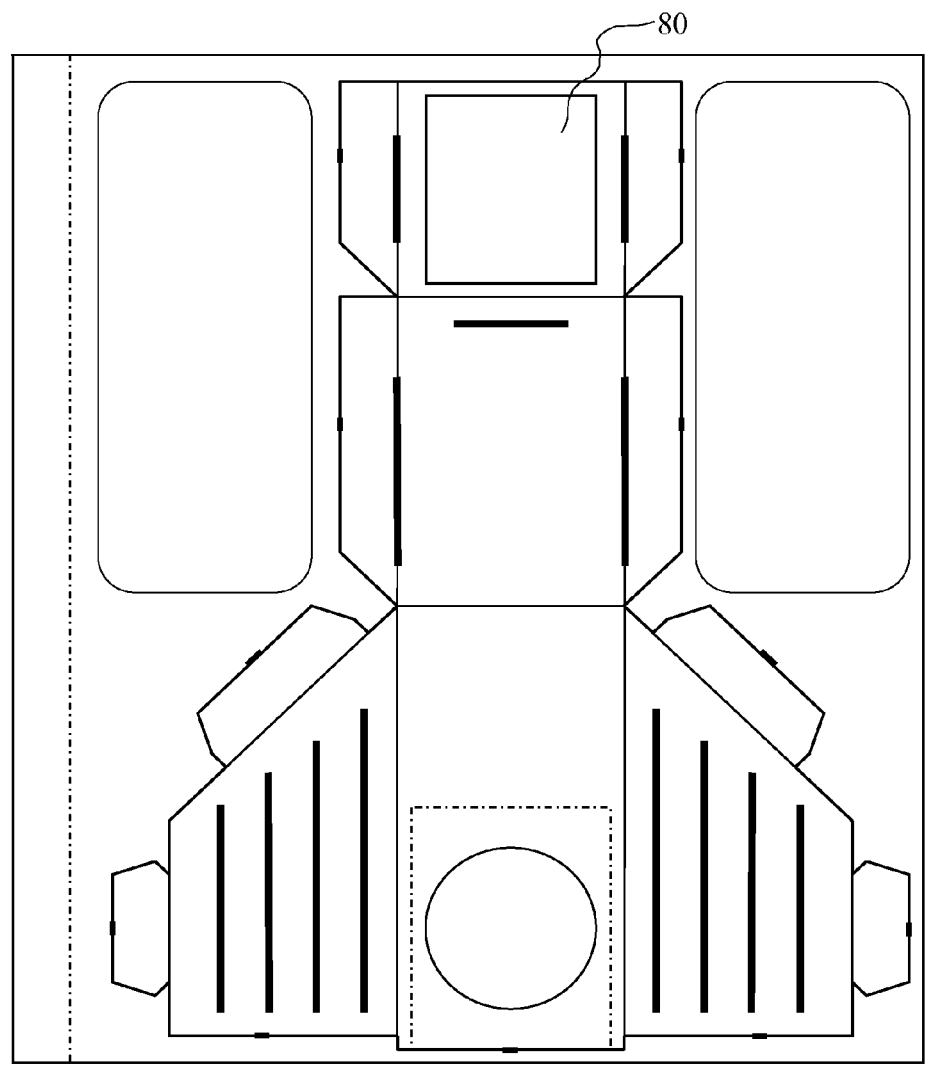
FIG. 11 illustrates a second flat deliverable alternative, external face.

FIG. 11 illustrates a second alternative which may be delivered flat, its external face.

In the example of this second alternative, the means for producing optical magnification of the image comprise a single Fresnel lens with a large surface area 80. In this alternative, the plane of the image to be acquired by the electronic appliance is not the one of the skin surface but that of the surface of the lens. In practice, at the natural shooting distance taking into account the size of the objects, the field depth of most of the appliances is sufficient so that the enlarged image and the skin surface which surrounds it are both sharp in the acquired image.

Figure 12:
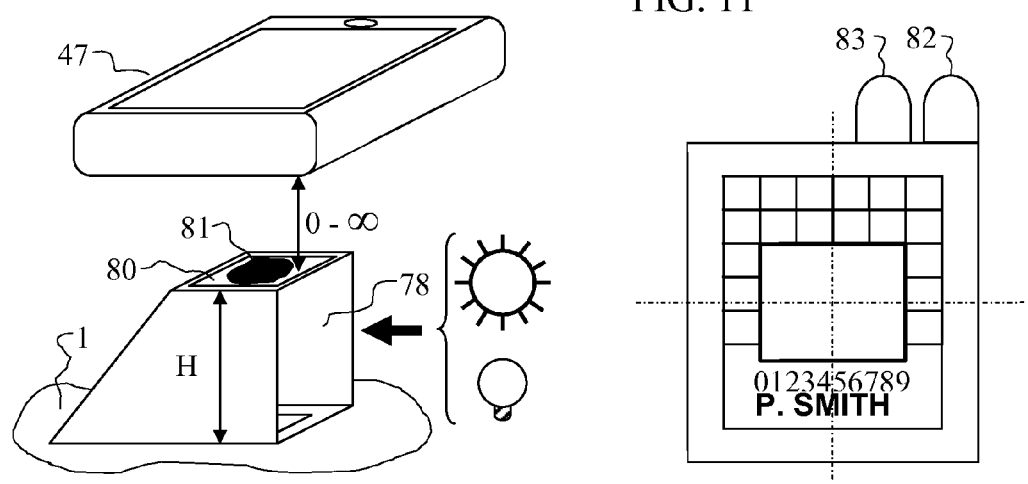
FIG. 12 illustrates the flat alternative of FIG. 11 in a real-life situation.

FIG. 12 illustrates the flat alternative of FIG. 11 in a real-life situation.

The Fresnel lens 80 is designed so as to make visible an enlarged image 81 of the skin surface 1 to be analyzed placed at a distance H from the lens. The distance H, set by design when the base of the device is in contact with the skin, determines the magnification. The distance H is determined so as to maximize the magnification while guaranteeing a sharp image and sufficient field depth. The lens, or the assembly of the lens if necessary, are laid out so that the enlarged image appearing in the plane of the lens is sharp independently of the distance at which is found the objective of the consumer electronics device used for acquiring the image.

Figure 13:
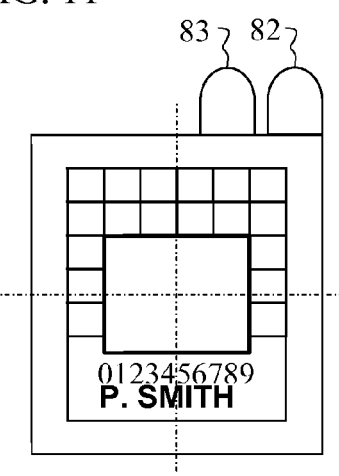
FIG. 13 illustrates consumable means for the second alternative.

FIG. 13 illustrates consumable means for the second alternative. The use of a Fresnel lens provides many advantages including that of lightness. The device of FIG. 11, entirely made in materials appearing as sheets, has a small mass. This small mass of the device makes it possible to maintain it temporarily in a functional position on the skin, regardless of its orientation, by adhesive means. A sub-assembly for single or limited use, said to be consumable, particularly suitable for this alternative of the device, is thereby provided. This consumable, in addition to the calibration and transformation functions according to the invention and the presence of a repositionable adhesive deposited on the face turned towards the lens in order to ensure its attachment under the base of the device, also comprises an adhesive for ensuring its attachment on the skin. A protective film 82 to be removed before use is provided on the face of the consumable on the side of the lens and another protective film 83 is provided on the side to be applied on the skin.

Figure 14:
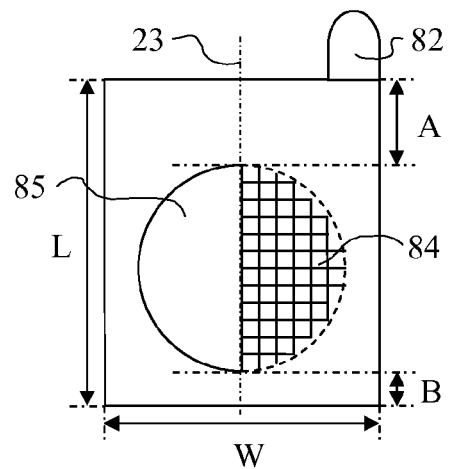
FIG. 14 illustrates means for calibrating the measurements and evaluations.

FIG. 14 illustrates means for calibrating the measurement or the evaluation of the characteristics of interest of the image and/or for transforming according to the invention the physical, chemical or biological characteristics of the skin so as to be able to appreciate them by image analysis. The purpose of the calibration is to get rid of all the errors and distortions introduced into the chain for acquiring and transmitting the image. The technical solution according to the invention consists of including in the field of acquisition of the image, elements, at least one characteristic of which is known. Thus the suitable image processing software packages have a reference in the image which allows them to correct the latter so as to again find the known value of the characteristic for the reference element. The correction giving the best result for the reference element is then applied to the remainder of the image. Refinements are provided in order to improve the accuracy of the corrections by taking into account the localization of the pixels and by knowing optical characteristics of the image-sharpening means according to the invention. The example shown illustrates the use of so-called consumable means for receiving the calibration elements and if necessary, conversion elements in the area 84. The presence of a regular grid in the area 84 is particularly advantageous. With the grid, it is possible to delimit with a strong contrast which facilitates the subsequent image processing operations, each area bearing determined colors and/or surfaces having brightness, i.e. a light reflection level, and/or reagents which change color under the reaction of a physical, chemical or biological characteristic of the skin. Further the grid gives the possibility of evaluating geometrical distortions of the type and intensity introduced by the optical components and of correcting them a posteriori by suitable image processing operations. With the grid it is further possible to more efficiently correct chromatic aberrations by executing suitable image processing operations, in that the grid appearing black gives the exact position of the pixels for which shifts are observed for certain components of their color and that consequently the suitable software packages perform inverse shifts and reconstruct the actual colors of the pixels of the whole of the image. Moreover, the grid marks in a more contrasted way, the limits of the areas comprising calibration and/or conversion elements, this improves the efficiency of the processing software packages which center the sampling of the pixels at the center of the relevant elementary boxes in order to eliminate any risk of perturbations at the boundaries of each area. Further, a grid is a pattern which may easily be reconstructed by software in the case of missing pixels by knowing its dimensions and its pitch which will be constant advantageously. The presence in the image of a grid of at least one elementary box, having known dimensions in abscissas and in ordinates as well as possibly having a controlled and known line width, further provides the advantage of allowing accurate measurement of the elements of the image by subsequent image processing without requiring large absolute accuracy in controlling the dimensional and optical characteristics of the means applied in the image acquisition chain. By knowing the actual dimensions of the elements of the image, it is further possible to put back a plurality of images to the same scale with view to their comparison. The comparison of the images, after possible complementary processing operations for translation and/or rotating the whole of the pixels of the image in order to bring back an element of interest to the same location of the image prepared with view to comparison and in an identical position for all the images, is advantageously accomplished by executing software packages for automatically comparing the images of a same object of interest such as a mole or a lesion. It is further provided that the comparison of the images may be accomplished with the human eye by simultaneously displaying the images on a screen, juxtaposed or superposed, notably with the purpose of checking a posteriori the reason of an alert having been automatically generated by the comparison means based on image processing software packages. The presence of reference elements in each image further allows old images to benefit from progress achieved in image processing operations by executing the new image processing operations on old images with view to analyzing new characteristics of the skin or to produce more accurate measurements of characteristics analyzed previously. The area 85 is pierced so as to show the skin surface in the field for acquiring the image. This example makes use of the symmetry along the main axis 23 as explained in FIG. 2. It is provided that the consumable means of FIG. 14 are fixed on the base of a device such as those of FIG. 2 or 5 by means of a repositionable adhesive protected by a removable film 82 unit until its use. Foolproofing is provided in order to prevent the user from getting the orientation wrong upon laying the consumable. A single position is possible, knowing that the adhesive is present on a single face in this alternative and that the positioning of the window is asymmetrical (the length L is different from the width W and the quantities A and B are different).

Figure 15:
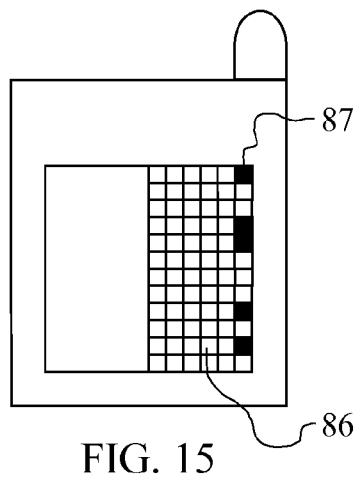
FIG. 15 illustrates another arrangement of the means of FIG. 14.

FIG. 15 illustrates another arrangement of the consumable means of FIG. 14. In this example, the analysis, calibration and if necessary conversion window is rectangular instead of being round, which maximizes the image surface area which may be used for calibration and/or conversion purposes. As a sufficient amount of elementary areas 86 for calibration are present in the image, it becomes possible to use elementary areas for coding the type of consumable and to know all its characteristics via a database. In this example, the elementary areas of the column 87, depending on whether they are white or black, code the reference of the consumable in binary code.

Figure 16:
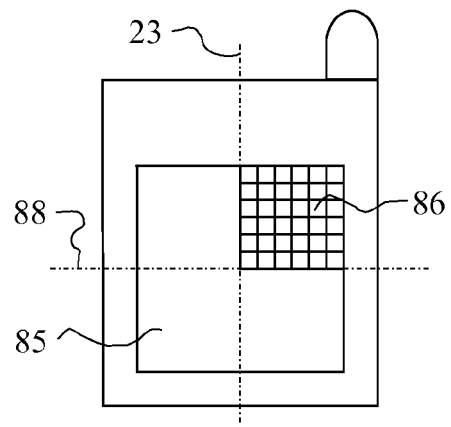
FIG. 16 illustrates the use of two axes of symmetry.

FIG. 16 illustrates the use of two axes of symmetry. This example takes advantage of the existence of a second axis of symmetry 88 which is perpendicular to the main axis of symmetry 23 and which cuts it in the center of the image. The second axis of symmetry thus also cuts the optical axis of the device according to the invention which is aligned on that of the electronic appliance. Exploitation of the second axis of symmetry is provided in order to increase the relative surface area in the image of the pierced area 85 exposing the skin. In this alternative, provision is made for taking into account the fact that the second axis of symmetry 88 is an axis of symmetry for the optical means but not for the light source. Thus, it is provided that the allocation of the elementary areas 86 takes this difference into account in order to obtain the best results. For example, the elementary areas allocated to the calibration of the rendering of the colors, the rendering of which does not depend on the luminosity will preferably be far from the center of the image so as to be able to bring other ones closer, the rendering of which may be influenced by changes in the illumination level, of the most homogeneous illumination areas.

Figure 17:
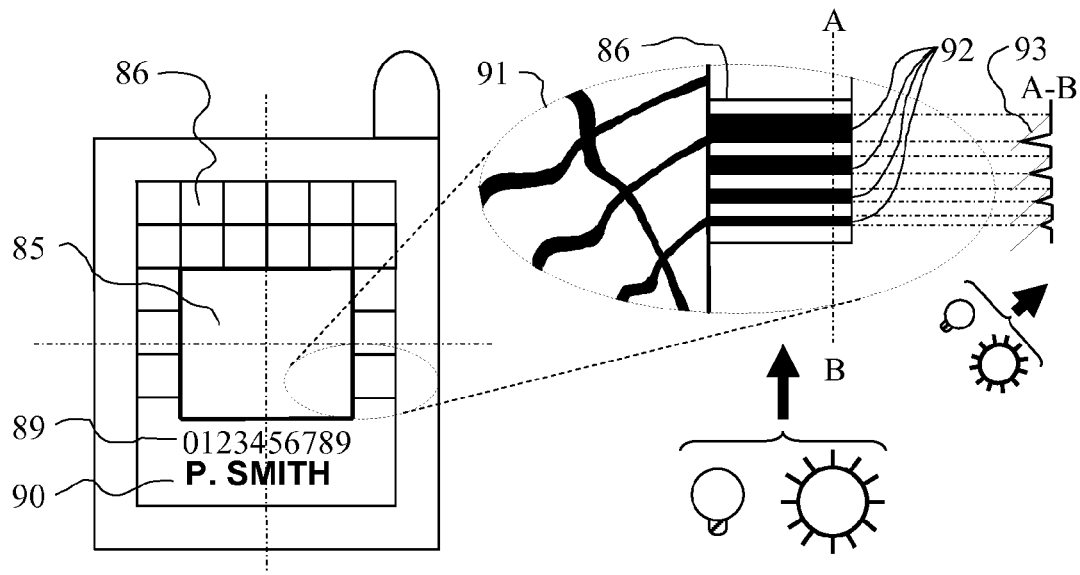
FIG. 17 illustrates an alternative consumable freeing the central area.

FIG. 17 illustrates a preferred consumable alternative which provides the advantage of allocating the central area of the image to the pierced portion 85 exposing the skin. This example assumes the use of optical means, the characteristics of which are known, characterized and reproducible. In the case of the use of optical means introducing defects in the image requiring correction, the characteristics of said optical means are identified by an identification means included in the image at the device itself (not shown in FIG. 17). In the case of the use of optical means which do not introduce any notable defects in the image or introduce known defects duly listed, these optical means are identifiable so as to be able to correct their defects without having to resort to calibration means present in the image. The defects which may be easily corrected in this way are geometrical distortions and aberrations of all types including vignetting. There just remains the need for calibrating the rendering of the colors and the sensitivity of the image acquisition chain. If necessary, means for converting physical, chemical or biological characteristics into a change of color of one or of several elementary areas may require calibration elements or controls which are specific to them. Under the conditions of this example, less elementary areas 86 are required for applying the invention and these areas are distributed around the pierced central area 85 exposing the skin.

It is provided that a decrease in the number of elementary areas with respect to the other previous alternatives be compensated by an increase in the number of references of consumables in order to be able to meet the whole of the needs. The characteristics of the consumable means are identified by an identification means 89 included in the image at the actual consumable which allows execution of suitable image processing operations. Generally the processing means execute a request in a database from the code 89 of the consumable, the base sending back the detailed characteristics of the consumable and, if necessary, information in connection with the corresponding processing operations. These pieces of information are for example the name of the processing program to be executed accompanied by suitable parameters or a complete program component ready to be executed. This consumable example further comprises an area 90 allowing the user to enter at least one piece of information into the image. In this example this is an area for freely writing a name for example, other alternatives are provided for making selections from closed proposal lists. The enlarged detail 91 more particularly illustrates the means which are advantageously applied for appreciating the skin relief according to the invention, i.e. by means mainly falling under optics and image processing operations. At least one elementary area 86 comprises raised portions 92 having known heights, said raised portions being laid out by order of increasing heights, the smallest height being the closest to the light source as is shown by the section A-B. The image processing operations for measuring the skin relief measure the width of the cast shadow under illumination mainly consisting of parallel rays tilted by a suitable angle 93. The measurement of the skin relief is accomplished after a calibration step which assumes as a reference said at least one elementary area comprising relief elements having known heights. In practice, a compromise should be found between the purity of the light illuminating the image to be acquired relatively to the parallel rays of interest and the amount of incoming light in order to obtain cast shadows having sufficient contrast for being utilized by the image processing operations.

Figure 18:
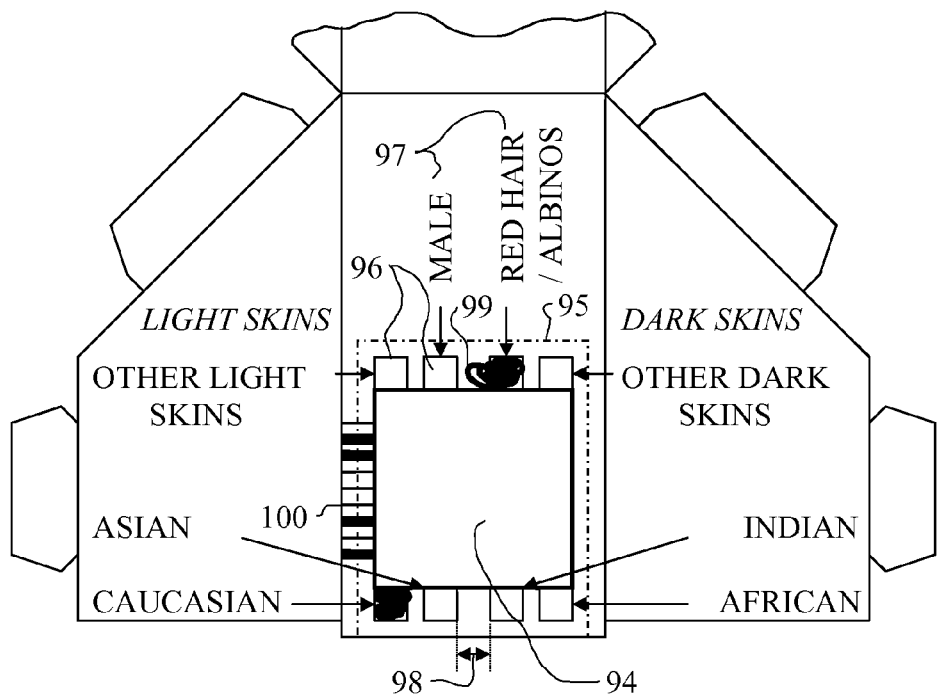
FIG. 18 illustrates means for entering information into the image.

FIG. 18 illustrates means for entering information in the image. This figure illustrates exemplary means for allowing the user to enter at least one piece of information into the image in the case of the alternative device of FIG. 5. This is particularly advantageous since the device of FIG. 5 which is delivered flat and which already comprises prints for other purposes, the additional cost for adding these information input means is zero. It is provided that the pierced area 94 in the base of the device (not to be mistaken with the pierced area 85 in a consumable) may have any shape, for example round in FIG. 5, rectangular in the example of FIG. 18. The cut-out area 94 is comprised in the frame 95 delimiting the image to be acquired. It is provided that the space comprised between the pierced area 94 and the frame 95 delimiting the image to be acquired, is occupied by delimited areas 96 which are associated with selections expressed in natural language 97 or by reference in a caption. It is provided that the areas to be blackened in order to express a selection are separated from each other by a space 98 for absorbing possible overflows 99 upon blackening an area 96 and avoiding that it is interpreted by the image processing operations as the blackening of an adjacent area. In certain alternatives, provision is also made for selecting a proposal by encircling the retained proposal with a line and/or by crossing out the rejected proposals. Means are also provided for identifying each alternative means for entering information by selection from closed lists. This may for example be a 1D barcode 100 as in this example or a more compact so-called 2D code, from direct use of alphanumerical characters as in FIG. 17, binary coding as in FIG. 15 or any other means for coding a reference in an image which may be subject to recognition and decoding by suitable processing of the image. It should be noted that elementary computer programs allowing recognition in an image of the value of a 1D or 2D barcode, a series of alphanumerical characters and many other coding means which may be utilized within the scope of the invention for the purposes of identifying alternative devices or consumables are comprised in the state of the art. In this example illustrating the case of a very low cost device, it is provided that it be a device for a single use or for an occasional use and in most cases for a single user. In this context, it is particularly relevant to use the printable surface of the inner face of the device, on which it is possible to write in order to enter information before its final assembly. In this example, the input of information by the user, indirectly describing the main characteristics of his/her skin by specifying the ethnic group to which he/she belongs, is particularly useful. By knowing the ethnic group, it is for example possible to refine the image processing operations and also obtain complementary information contained in databases which associate characteristics of the skin with genetic characters in connection with the ethnic group type of the persons. In this example, the image processing operations, which are aware of the proposed selections and of their localization after reading the code 100 and querying the corresponding database, decode that the user is a woman of the Caucasian type having a red head skin.

Figure 19:
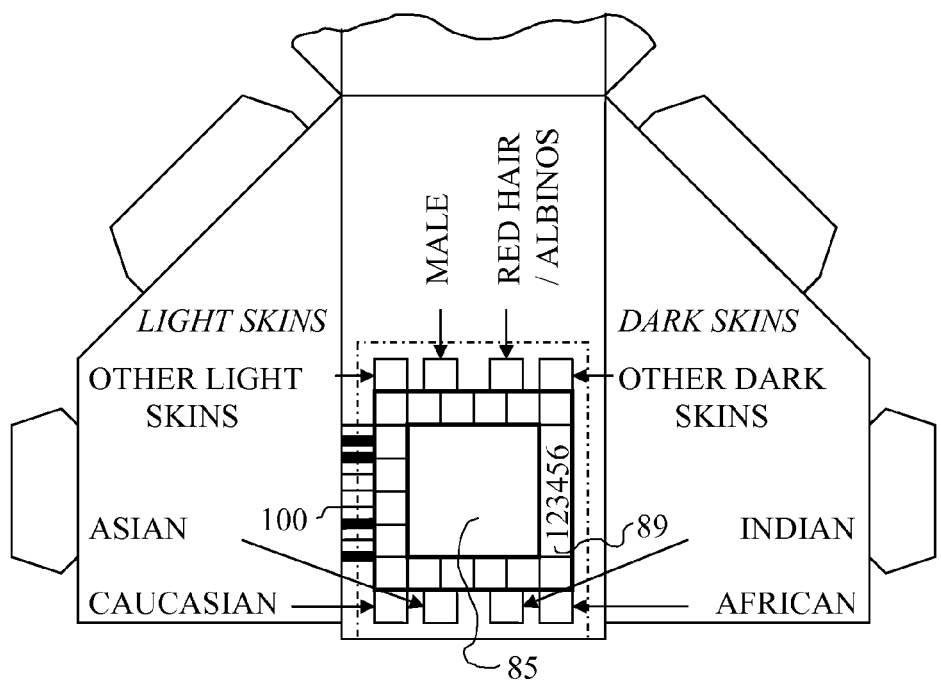
FIG. 19 illustrates the means of FIG. 18 with a consumable.

FIG. 19 illustrates the means of FIG. 18 under the base of which a suitable consumable has been adhered in order to ensure calibration of the image processing operations and/or conversion of physical, chemical or biological parameters. In this example, the means for entering at least one piece of information are identified by a code 100 and the consumable is identified by a code 89. The skin surface to be analyzed appears in the pierced area 85 of the consumable. Of course, there is no departure from the scope of the invention if the calibration and/or conversion means are directly deposited on the internal face of the device instead of being deposited on replaceable so-called consumable means.

Figure 20:
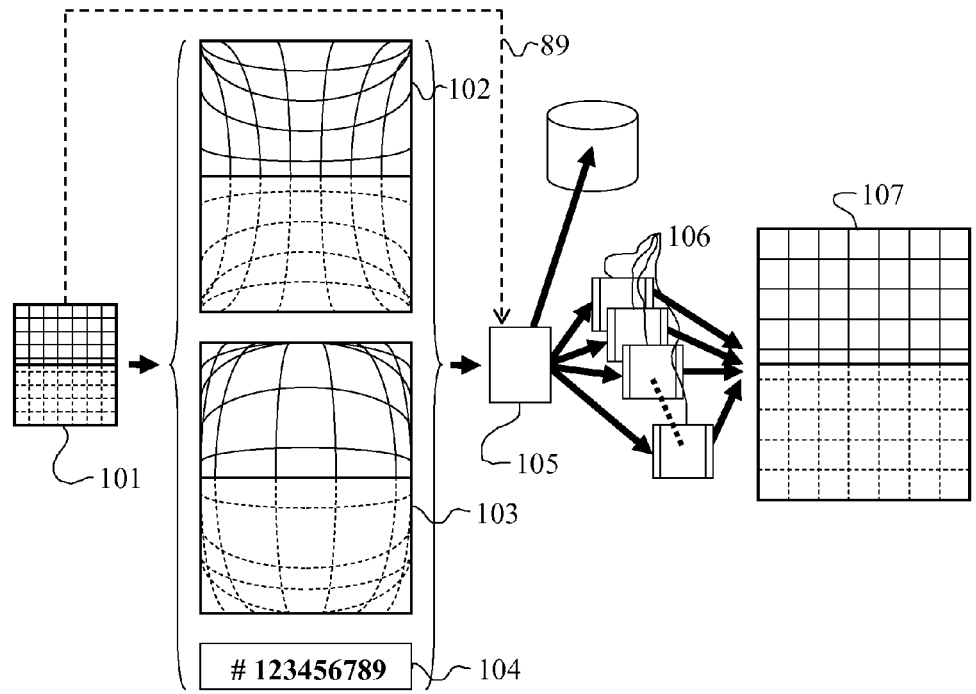
FIG. 20 illustrates image processing operations for correcting distortions.

FIG. 20 illustrates image processing operations for correcting geometrical distortions in the case of the use of low cost optical means. Simplified optics with a single lens, in particular when this is a so-called Fresnel lens, made with materials and with low cost methods is capable of introducing geometrical distortions. For example, these may be so-called pin cushion distortions or barrel-shaped distortions which deform the image of a regular grid 101 like in the representations 102 or 103, respectively. In certain alternatives, provision is advantageously made not for seeking optics which does not deform the image but for making, in a reproducible way, optics which deform the image in a known way. The correction is then accomplished by applying a suitable processing profile called up according to an identifier of the optics 104. Provision is also made for another approach which is based on image processing operations which are capable of correcting all or part of the distortions and aberrations without it being necessary that they be aware of the characteristics of the optics or of possibly those of the grid 89. Each approach having its advantages and its drawbacks, by knowing the characteristics of the optics, it is generally possible to simplify the image processing programs and to reduce the execution times to the expense of managing additional information. Provision is made for arbitrating between the different previous options depending on hardware and economical constraints upon applying the invention. In this non-limiting example, a first processing operation 105 stores and indexes the acquired raw image in a database and then calls up the elementary image processing operation(s) 106 corresponding to the distortions to be corrected in order to produce data coding a resulting image 107 in which the geometrical distortions have been corrected. It is possible to apply the invention by storing the corrected images rather than the raw images, this being the case, it will generally be preferred when data processing power is not considered as a rare resource, to store the raw images in order not to lose any information and to be able to benefit from the continuous improvements of image processing computer programs. It is thus preferred at each new need to again process old images with the last versions of the available image processing programs.

Figure 21:
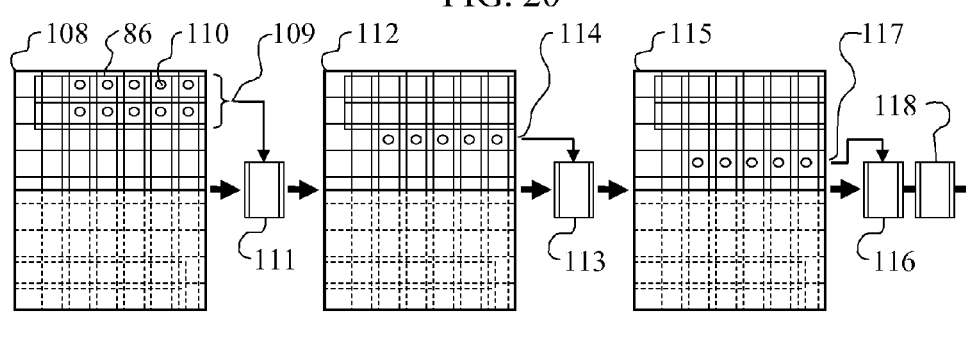
FIG. 21 illustrates processing operations for calibration, correction and transformation.
Figure 21:
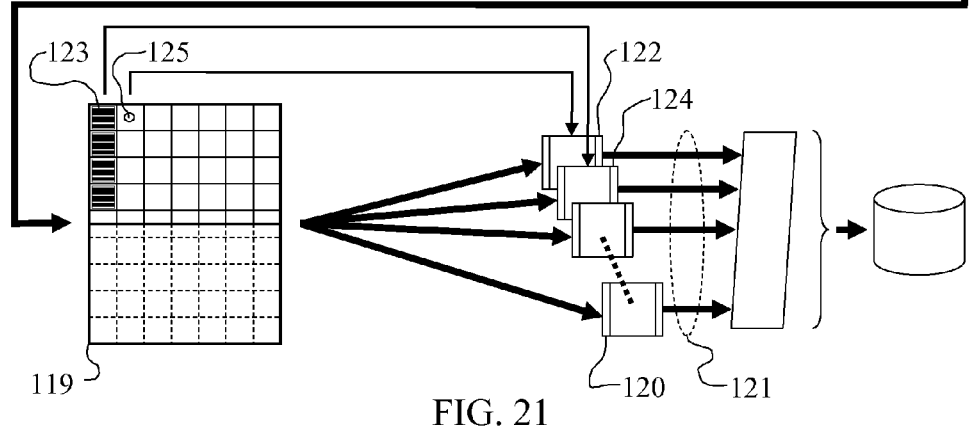

FIG. 21 illustrates image processing operations for calibrating the characteristics of the image, for correcting chromatic aberrations, for evaluating characteristics of the skin via characteristics of the image which vary depending on the characteristics of the skin.

This exemplary application of the method according to the invention illustrates image processing operations executed sequentially or in parallel depending on the cases, the first image 108 in this processing chain is advantageously the one which stems from a preliminary step for correcting geometrical distortions (advantageously the image 108 is the image 107 of FIG. 20). A step aiming at calibrating the rendering of the colors uses color references of the first two lines 109. In order to avoid being subject to the effect of possible chromatic aberrations which have not yet been corrected, the color references taken into account are those of groups of pixels 110 far away from the edges of the elementary areas 86. In addition to the three pure fundamental colors, yellow, magenta and cyan plus black and white, a typical chart of skin colors will advantageously be added, taking into account the relevant relatively limited range of colors and the delicacy of the hues to be discriminated within this range. The execution of the processing operation 111 produces an intermediate image 112, for which the color of each pixel has been corrected according to the initial rendering of the reference colors 109.

The following processing operation 113 aims at correcting the vignetting and/or the affect of a non-homogeneous distribution of the light on the surface of the image to be acquired. The correction is based on identical color and brightness references, for example satin white corresponding to the middle of a brightness scale. The elementary areas receiving the reference color for this image processing operation will suitably be distributed depending on the characteristics of the illumination means, for example continuously on all the elementary areas of a line 114 parallel to the axis of symmetry of the light source and not too far from the center of the image. At the end of the processing operation 113, an intermediate image 115 is produced in which the luminosity of the pixels has been corrected according to the initial rendering of the identical references depending on their localization and by, if necessary, taking into account light distribution laws of optical means used for the pixels far away from the reference areas and from their symmetrical areas relatively to at least one axis of symmetry.

The following processing operation 116 aims at calibrating the rendering of brightness relatively to the brightness range which may be encountered as regards human skin in order to be able to utilize at best the dynamics of the image acquisition chain according to this criterion. The correction is based on references 117 for example comprising a few elementary areas, each having a different but realistic brightness level, and the same color such as beige corresponding to a skin of average tonality. An area of one color corresponding to a realistic mat black skin and an area of one color corresponding to a realistic pale and fat skin will advantageously be added, this for calibrating the extreme values. Processing 118 for correcting chromatic aberrations is advantageously applied to the image stemming from the processing operation 116 in order to produce a corrected and calibrated image 119 suitable for the execution of processing operations 120 aiming at analyzing characteristics of the skin strictly speaking, i.e. processing operations aiming at producing quantitative data 121 and/or qualitative indications in connection with characteristics of the skin.

The characteristics of interest for which suitable image processing operations are executed depend on the field of application of the invention.

For example in the field of cosmetics, it is desirable to characterize the analyzed skin as regards:
color,
brightness,
surface humidity,
texture,
skin relief,
pigmentation,
elasticity,
the presence of wrinkles,
the presence of keratin,
the presence of impurities,
the presence of visible pores or lesions,
the size, the number of pores visible per unit surface,
surface acidity,
sensitivity to certain products,
the type of microbial flora colonizing the surface etc.

In the example of FIG. 21, a processing operation 122 based on calibration information of the column 123 aims at quantifying the skin relief.

An image processing operation 124 is based on the color of the elementary area 125 which corresponds to the image seen by transparency of a reagent which is printed on the face of the consumable which comes into contact with the skin during the acquisition of the image, said consumable consisting of a transparent plastic material sheet on which the different colors and reagents are deposited for example by using conventional pad printing or screen printing methods on one face and/or on the other one depending on their function. This reagent changes from intense blue to bright pink depending on the humidity percentage at the surface of the skin. Provision is made for applying this same technical solution with different reagents placed in other elementary areas of the consumable in order to evaluate other physical, chemical or biological characteristics of the skin.

The data 121 produced by the means and methods according to the invention are then capable of being stored and/or utilized by any method of a higher order.

Figure 22:
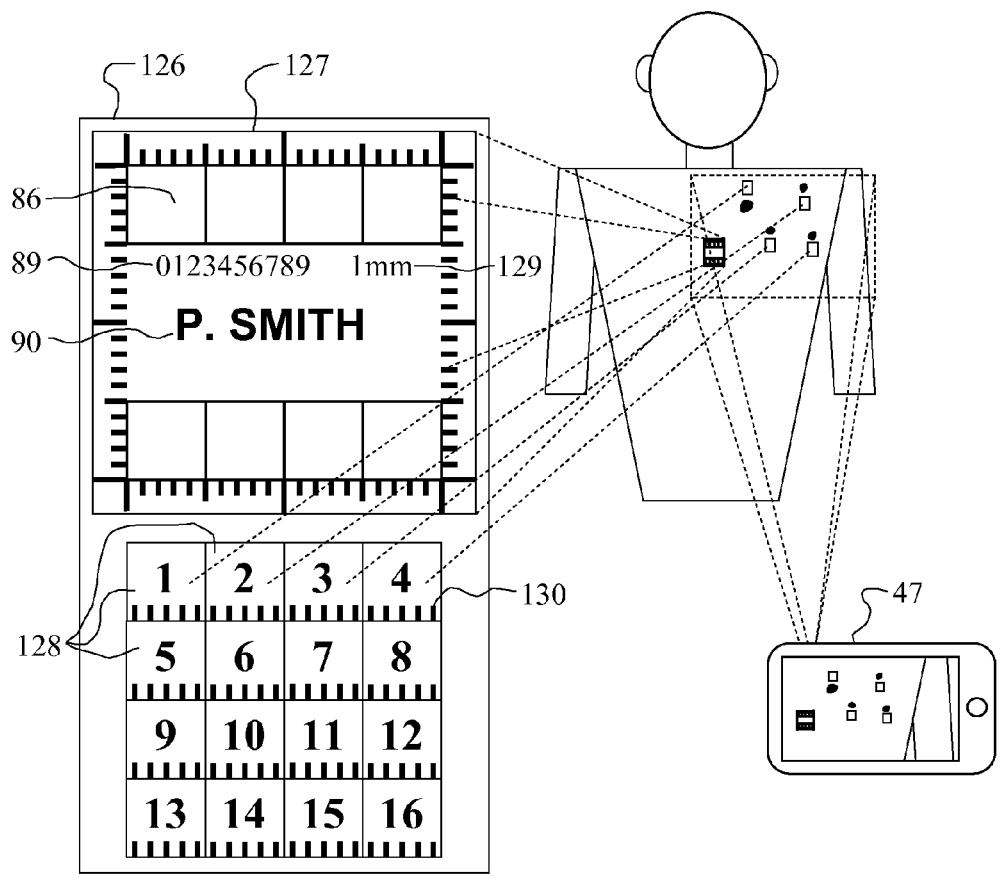
FIG. 22 illustrates a use for detecting skin cancer.

FIG. 22 illustrates a use of the invention in the field of detecting skin cancer.

A first problem consists of making an inventory and a list of the moles and lesions to be monitored, being aware that generally a person has several of them distributed on skin surfaces which may be relatively large, for example on all the top of the back. A consumable 126 is provided in the form of a sheet comprising several self-adhesive elements (127, 128) using an adhesive with an average adhesion force, which may be repositioned several times, and able to be in contact with the skin. A first element 127 of the consumable of FIG. 22 is a means for introducing into the image to be acquired, dimensional references in abscissas and ordinates. The graduation unit is for example the millimeter and it is explicitly indicated advantageously 129. Advantageously an area 90 is made for allowing the input of at least one piece of information by the user such as a name, a date. An identification code 89 of the consumable as well as elementary calibration and/or conversion areas 86 are provided in certain alternatives. It is provided that the consumable further comprises a plurality of numbered self-adhesive labels 128. These labels 128 advantageously comprise also dimensional references 130 in one or in two dimensions.

The invention utilizes in this alternative the native capacity of consumer electronics devices 47 for acquiring images of a large skin surface in order to reference each mole and/or lesion to be monitored by a number by means of numbered self-adhesive labels 128 being part of the consumable means 126 provided for the application of the invention.

The resulting overall digital image(s) are stored in memory in data storage means, either local or remote, and/or printed in order to keep in memory the number of each mole or of each lesion in order to be able to track its development over time. Moreover, certain particularly performing electronic appliance versions, having high resolution and a capability of close focusing of the macrophotographic type, allows the application of the invention without requiring any complementary means for producing optical magnification and for sharpening the image at a closer distance than that authorized by the native optical means of the device.

Figures 23, 24:
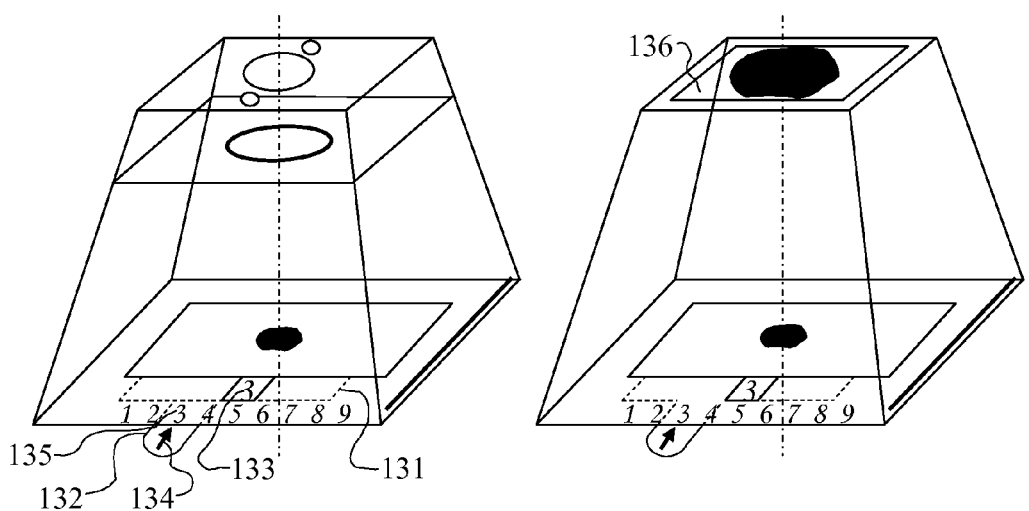
FIG. 23 illustrates a refinement of the first alternative of the device.
FIG. 24 illustrates the refinement of FIG. 23 for the second alternative.

FIG. 23 illustrates a functional refinement of said first alternative of the device according to the invention. The means for producing optical magnification and for sharpening the image at a closer distance than the one allowed by the native optical means of the device, are advantageously completed by means for perennially including in the image the number associated with the mole or the lesion for which acquisition of a close and enlarged image is desired. FIG. 23 illustrates an exemplary mechanical solution based on a ruler 131 placed under the base of the device and translationally displaceable by the user by means of a tab 132. A window 133 discloses the number selected in the field of the image. Advantageously, an index 134 firmly attached to the tab 132 and which points towards a printed number 135 on an external face of the device, clearly indicates to the user the number 133 which appears in the window inside the device. Thus, the user may regularly acquire accurate images of each object of interest on his/her skin without any difficulty or risk of error on the objects by including the number 133 in the image. At each new image acquisition, the user recalls the overall image(s) acquired beforehand in order to again note for certain the number allocated to each object of interest. The system according to the invention, which for a given user advantageously keeps in memory the overall image(s) acquired beforehand, may provide him/her on his/her demand with these overall image(s) when desired via an electronic display or printing means available to the user. Further, it is provided that in the system according to the invention, processing operations for automatically indexing the images object by object depending on their number and associating them with the so-called overall image(s).

FIG. 24 illustrates the functional refinement of FIG. 23 transposed into the context of said second alternative of the device according to the invention which comprises means 136 for producing optical magnification and for sharpening the image independently of the distance at which is found the object of the consumer electronics device used for acquiring the image.

Figure 25:
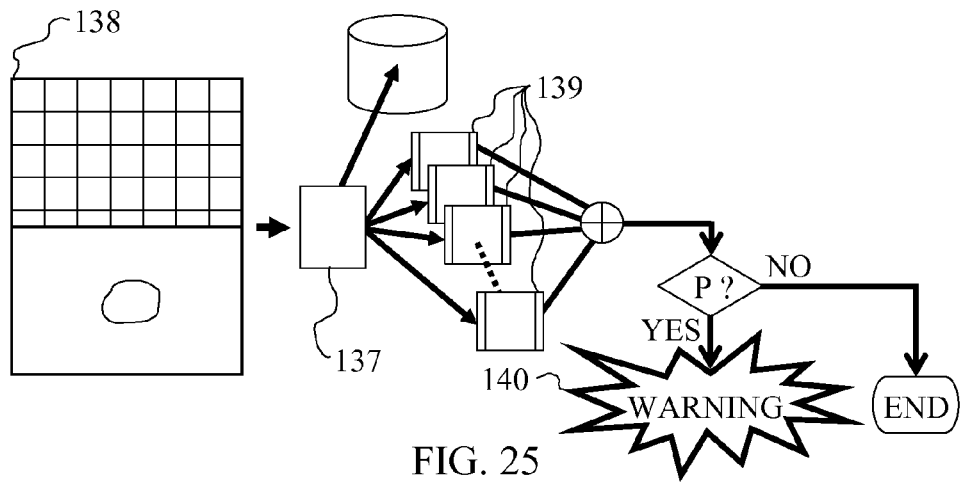
FIG. 25 illustrates the detection by processing operations on isolated images.

FIG. 25 illustrates the detection of problems by image processing operations on isolated images. Within the field of early detection of skin cancer, provision is made for executing processing operations on images of moles or lesions in order to detect the following signs which are recognized as relevant by dermatologists:
  black color appearing in the lesion,
  a shape which becomes asymmetrical,
  irregular edges,
  non-homogeneous coloration,
  large diameter (greater than 6 mm),
  time-dependent development of the lesion.

As regards image processing according to the invention, a distinction is made between a first group of image processing operations said to be on an isolated image which are executed image by image and a second group of processing operations said to be on multiple images which are executed on a plurality of images of the same objects of interest acquired at different instants. Naturally, it is provided that all the images on which processing operations are applied on multiple images have been subject beforehand to image processing operations on an isolated image.

Preliminary processing operations 137 such as storage in a database, correction and/or calibration and/or transformation processing operations according to the invention such as those described earlier, are applied to an image 138. The resulting image is subject to a battery of specialized processing operations 139 with the purpose of searching for at least the first five signs of the previous list. It is provided that a problem be detected 140 and reported to a process of higher order if at least one relevant sign was detected at the end of the corresponding processing operation.

Figure 26:
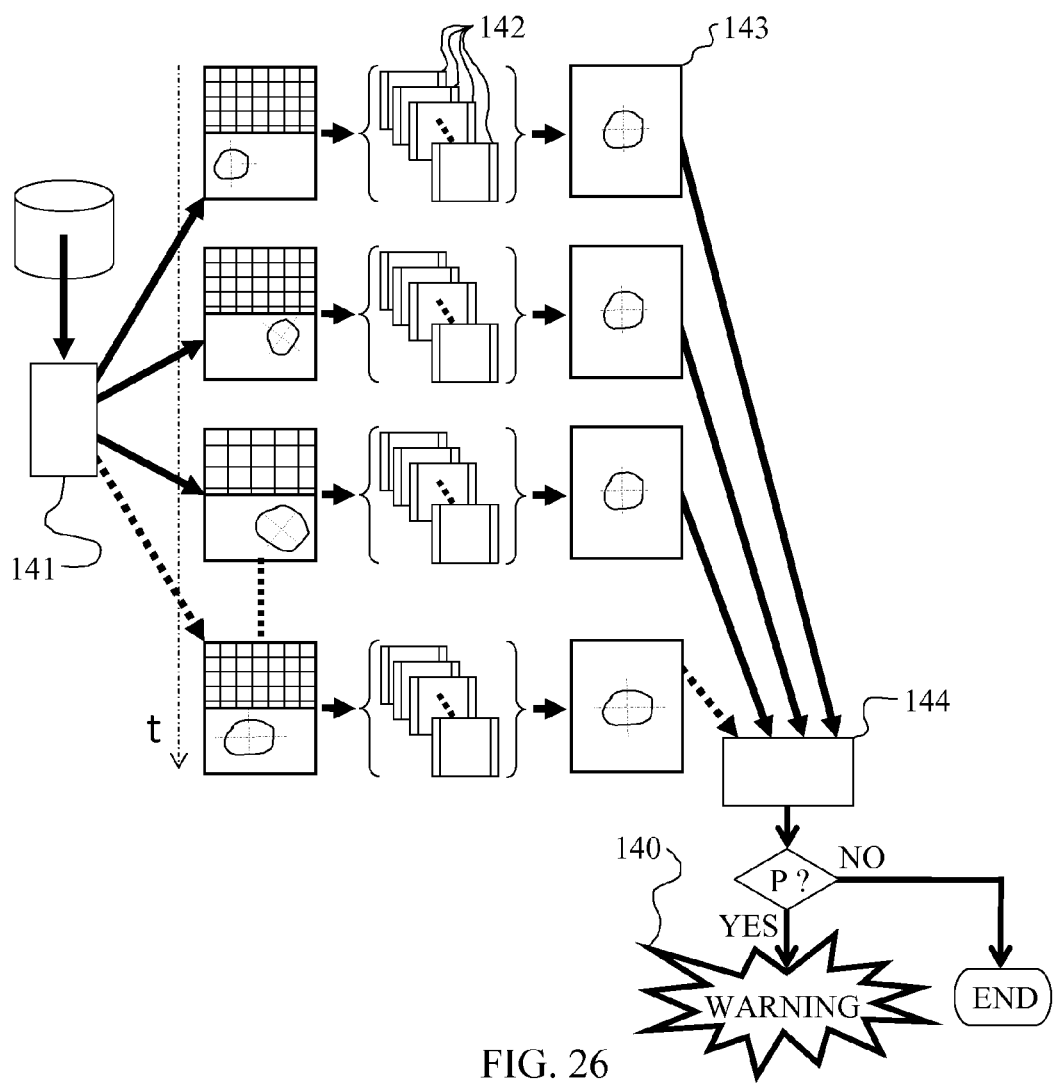
FIG. 26 illustrates the detection by processing operations on multiple images.

FIG. 26 illustrates the detection of problems by image processing operations said to be on multiple images. Images acquired beforehand are, if necessary, subject to correction and/or calibration and/or transformation processing operations 141 according to the invention as described earlier. The images are further ordered depending on the time stamp of their acquisition for example by means of information associated with the file system or contained in metadata associated with each digital image. The resulting images are then subject to processing operations 142 aiming at normalizing them prior to the application of comparison processing operations. By normalizing the images is meant applying to the pixels of these images, processing operations such as translations and/or rotations aiming at centering the object of interest and at orienting it identically in the plane of the image, homothetic size reductions or increases for setting a common scale for the images to be compared. At the end of these preparatory processing operations, the resulting images 143 of the same object acquired at different instants are identical, within a tolerance which is advantageously determined by the system in a self-adaptive way, as long as the mole or the lesion does not develop abnormally. It is provided that a problem be detected 140 and reported to a process of higher order if the abnormal change is detected following the execution of suitable processing operations 144.

With time-scheduling prior to the application of the comparison processing operations 144, it is possible to simplify them in that what is sought for detecting an abnormality is the increase of at least one characteristic of the image relatively to an image acquired previously. Further, by managing the instants for acquiring the images, it is advantageously possible to calculate development rates and to enrich with these complementary pieces of information, the information for reporting detection of a problem to the process of higher order. For example actions are provided which utilize the complementary information on the development rate in order to optimize the management of the urgency degree for consulting a physician after the detection of a problem.

Figure 27:
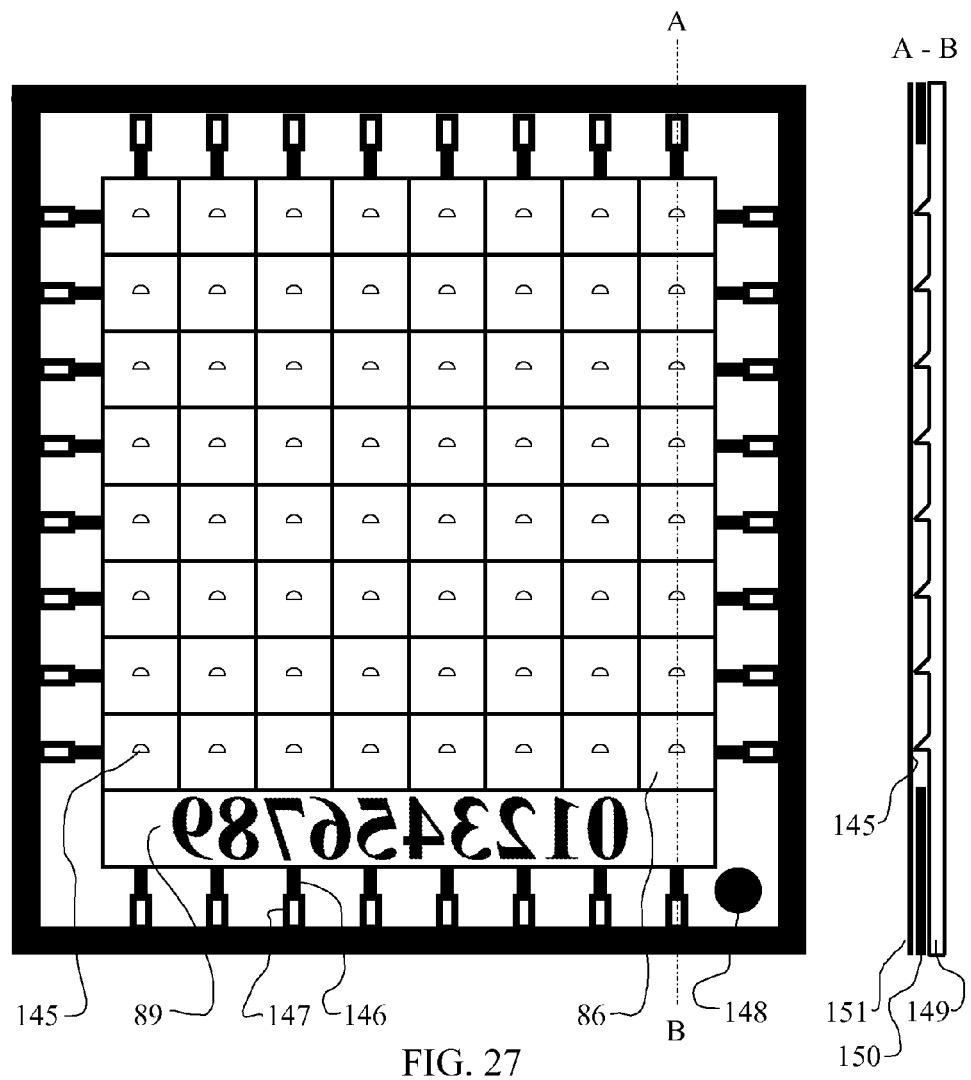
FIG. 27 illustrates a consumable for allergenic substances.

FIG. 27 illustrates an exemplary consumable used for searching for allergenic substances according to the invention. The consumable subset of this non-limiting example is seen from below. The consumable advantageously comprises the largest number as possible of elementary areas 86, in a surface provided in order to be used as a consumable associated with means for producing optical magnification of the image according to the invention as described in the previous examples. It is also preferably provided that the consumables for searching for allergenic substances be suitable for image acquisition by a consumer electronics device without it being necessary to use means for producing optical magnification of the image. An increase in the surface area of the consumable is provided in order to be able to do without additional means for magnifying the image. Each of the elementary areas 86 comprises at least one microstrip 145 or microtip on which is deposited a possibly allergenic substance. Means are provided for depositing on the skin, marks allowing the image processing operations to localize the location where each microstrip 145 or microtip has caused a microlesion of the skin during the application. Advantageously with the purpose of increasing the density of elementary areas per consumable, the whole of the grid will not be materialized but only the peripheral marks (146, 147) will be materialized. In order to allow the image processing operations to locate the localization elements regardless of the color of the skin on which they are applied, a dark marking 146 will systematically be associated with a pale marking 147. At least one global orientation mark 148 of the consumable will advantageously be added in order to allow the image processing operations to adapt to the positioning of the image of the consumable in the image as acquired by the electronic appliance. An identification code 89 of the consumable is required so that the substances causing a skin reaction are identified by the processing operations. The section A-B illustrates the internal structure of the consumable which comprises three distinct layers in this example. The main layer is the support 149 of the consumable which is made in a flexible plastic material of small thickness. The support 149 comprises at the center of each elementary area, at least one microstrip 145 or microtip for example formed during the molding of the support. Certain microstrip or microtip versions further comprise a microreservoir function in their center. The plastic material is treated if necessary, at least at the microstrips or microtips, so that the deposited substances adhere thereto. Solutions for adhering the substances founded, based on capillarity are also provided. The layer 150 is the layer which ensures adhesion on the skin of the whole of the consumable during the steps for application and for awaiting the reaction time of the immune system for possibly causing a visible skin reaction. When the minimum prescribed time has elapsed for a skin reaction to appear and before it is likely to disappear, the support 149 is detached from the layer 150 by means of a non-adhering wedge or a tab to be lifted. By withdrawing the support 149, all the areas which have been exposed to the substances as well as the marking elements indispensable for the following steps, will then appear. The layer 150 is made in an openworked flexible plastic material film according to the alternatives, completely in its center or preferentially only at each elementary area in order to achieve sealed partitions among them, avoiding possibilities of migrations and of mixings of substances between adjacent elementary areas. The film of the layer 150 is covered with suitable adhesives on both of its faces so that the adherence on the skin is stronger than on the plastic material of the support 149. Thus, the support may easily be detached without detaching the layer 150 from the skin. During the method for manufacturing the consumable, the substances to be caused to penetrate under the protective barrier of the skin are deposited on the microstrips or microtips after assembling the layer 150 on the support 149. The protective film 151 is then laid on the face of the layer 150 opposite to the support 149. The protective film 151 in plastic material closes the thereby formed assembly of the consumable so as to be impervious to air and to pollutants of any kinds. In the preferred alternatives where a partitioning is left between the elementary areas by suitable cutouts in the layer 150, each elementary area is then closed by the protective film forming an entirely impervious individual mini-box. After the image acquisition, the layer 150 may then be detached from the skin by means of a wedge left to be non-adhering or a tab distinct from those assigned to the detachment of the support 149. In low cost alternative embodiments, the layer 150 may advantageously use solutions for temporary marking of the skin by transfer, which are customarily used for making temporary tattoos.

Figure 28:
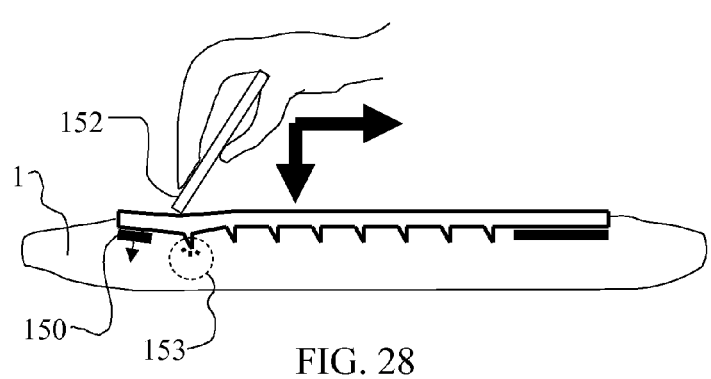
FIG. 28 illustrates the laying of the consumable for allergenic substances.

FIG. 28 illustrates the laying of the consumable used for seeking allergenic substances on the skin surface 1 by means of a small palette 152, made in rigid plastic material, with a rectangular shape and having a width corresponding to that of the consumable. The palette is systematically provided with the consumable. The laying consists of sweeping with the palette 152 the whole length of the consumable by continuously applying a force in the direction of the skin. This force generates pressure under the contact line between the palette and the support 149, which leads the microstrips 145 or microtips which are present under the line of application of the force, to causing microlesions 153 of the skin and having substances penetrate under the protection barrier of the skin. Application of the force during the sweeping of the surface of the consumable further ensures good adhesion of the layer 150 on the skin or, possibly a transfer of the film in the case of the use of solutions of the temporary tattooing type.

Of course, the invention is not limited to the examples which have just been described and many adjustments may be brought to these examples, notably by combining in a different way, elements taken from several examples, without departing from the scope of the invention.

A system for detecting the sensitivity of a person to one or several possibly allergenic substances by means falling under optics (4, 3) and data processing (4, 5) of images of the skin (1), characterized in that it comprises:
A consumable comprising one or more possibly allergenic substances to be put into contact with a skin surface; and
a consumer electronics device (4), able to acquire at least one image by digital means and able to produce data in connection with said at least one acquired image; and
means (4, 5) for processing said data in connection with said at least one acquired image with the purpose of producing information in relation with the sensitivity of a person to one or more possibly allergenic substances.

A system, characterized in that the consumable comprises at least two portions which may be separately withdrawn from the skin surface.

A system characterized in that the consumable further comprises means for including at least one visible mark in the image to be acquired.

A system, characterized in that the consumable further comprises means for causing at least one microlesion of the skin.

A system, characterized in that the consumable comprises a plurality of organized elementary areas in order to be able to determine the position thereof in the acquired image by image processing and/or by calculation.

A system, characterized in that it further comprises means for producing optical magnification of the image (7).

A system, characterized in that the means for producing optical magnification of the image further comprise:
means for sharpening the image during an image acquisition at a shorter distance than the shortest distance possible for which said consumer electronics device has been designed; and
means for temporarily attaching said means for sharpening the image on said consumer electronics device so that the image-sharpening means are placed suitably with respect to the objective of the consumer electronics device.

A system, characterized in that the means for producing optical magnification of the image further comprise:

means for sharpening the image independently of the distance at which is found the objective of the consumer electronics device used for acquiring the image; and means for temporarily maintaining the means for sharpening the image in a functional position on the skin.

A system, characterized in that the means for producing optical magnification of the image further comprise means for determining the focusing distance by contact between a hardware element and a portion of the body of the person, of whom the sensitivity to one or more possibly allergenic substances is desirably detected.

A system, characterized in that the consumable and/or the means for producing optical magnification of the image have characteristics which may be identified by an identification means included in the image.

A system, characterized in that the consumable and/or the means for producing optical magnification of the image further comprise means for allowing the user to enter at least one piece of information into the image.

A system, characterized in that the consumable and/or the means for producing optical magnification of the image further comprise means for calibrating at least one characteristic of the image.

A system, characterized in that the consumable and/or the means for producing optical magnification of the image further comprise means for providing at least one piece of information to the user.

A system, characterized in that the consumable and/or the means for producing optical magnification of the image are laid out so as to be delivered to the users in a form with small thickness using flexible materials.

A method for detecting the sensitivity of a person to one or more possibly allergenic substances by means falling under optics and data processing of a skin image, characterized in that it comprises steps during which:

a skin surface is put into contact with one or more possibly allergenic substances via a consumable; and at least one digital image is acquired, comprising a skin surface having been put into contact with one or more possibly allergenic substances by means of a consumer electronics device; and data related to said at least one acquired image are recovered in a format suitable for image processing operations; and the recovered data are processed, those which are in connection with the acquired image for producing at least one piece of information in relation with the sensitivity of a person to one or more possibly allergenic substances.

A method for detecting the sensitivity of a person to one or more possibly allergenic substances, characterized in that it further comprises a step during which means are placed for producing optical magnification of the image before its acquisition between the objective of said consumer electronics device and the skin surface.

A method for detecting the sensitivity of a person to one or more possibly allergenic substances, characterized in that it further comprises a step during which before the acquisition of said at least one image, at least one portion of the consumable is withdrawn after the minimum time required for a skin reaction to appear and before it is likely to disappear.

A method for detecting the sensitivity of a person to one or more possibly allergenic substances, characterized in that it further comprises a step during which said at least one image of the skin as acquired by means of a consumer electronics device and/or the data from the processing of said at least one image are corrected according to calibration information which is introduced into the image by the consumable and/or by the means for producing optical magnification of the image.

A method for detecting the sensitivity of a person to one or more possibly allergenic substances, characterized in that it further comprises a step during which the presence or the absence of a visible skin reaction is detected by a change of color and/or by a change of skin relief localized at the location of contact with the possibly allergenic substance.

A method for detecting the sensitivity of a person to one or more possibly allergenic substances, characterized in that it further comprises a step during which a comparison is made between the localization information of a skin reaction visible in an image, the knowledge of the corresponding localization on the consumable of the substance having caused the skin reaction and the knowledge of the nature of the substance which was deposited at the corresponding location on the consumable, in order to produce at least one piece of information in relation with the nature of the substance having caused the skin reaction.

A method for detecting the sensitivity of a person to one or more possibly allergenic substances, characterized in that it further comprises a step during which at least one piece of information is transmitted to a remote server from a consumer electronics device connected to a network.

A method for detecting the sensitivity of a person to one or more possibly allergenic substances, characterized in that it further comprises a step during which at least one portion of the expected results by receiving at least one piece of information from at least one remote server is handed over to the user.

The invention claimed is:

1. A system for analyzing a characteristic of skin, comprising:

a consumer electronics device comprising an objective and configured to i) digitally acquire an image of the skin from light reflected off skin being imaged, and ii) produce data representing the acquired image of the skin;

a first device comprising i) a first region to be placed at a distance between 0 and 50 mm of the skin being imaged, ii) a second region opposite the first region in a light path of the light reflected off the skin being imaged by the consumer electronics device, second region being placed at a distance between 0 and 2 meters of the objective of the consumer electronics device, the first device being placed in the optical axis of the objective of the consumer electronics device to allow the consumer electronics device to acquire the image the skin, and iii) an optical magnification element, distinct of the objective of said consumer electronics device, positioned in the light path between a) first region of the first device, and b) the second region of the first device, including the limits, the optical magnification element configured to optically bend or focus the light in the light path, before the light reaches the objective and the image is acquired by the consumer electronics device, the optical magnification element producing a global optical magnification of the image at a level suitable for analyzing the skin based on the data produced by the consumer electronics device; and a digital image processing device operatively connected to said consumer electronics device to i) receive said produced data of the acquired image of the skin, said produced data of the skin including data relating to additional visible information included in the image, and ii) process the received data of the acquired image of the skin to produce information in relation to at least one characteristic of the skin.

2. The system according to claim 1, wherein said optical magnification element optically bends or focuses the light for increasing said optical magnification of the image at a level suitable for analyzing hair.

3. The system according to claim 1, wherein said first device further comprises:
   a visual information display, including either of 2D or 3D identification or address code, alphanumeric or graphic element, in the area being imaged to be exploited by image processing.

4. The system according to claim 1, wherein said first device further comprising at least one consumable part.

5. The system according to claim 4, wherein said at least one consumable part comprises identification information in the area being imaged to be exploited by image processing.

6. The system according to claim 1,
   wherein said first device further comprises:
   an optical lens for sharpening the image during an image acquisition at a shorter distance than the shortest distance possible for which said consumer electronics device was designed; and
   a non-permanent connection for temporarily attaching said first device onto said consumer electronics device so that the optical lens are suitably placed relatively to the objective of the consumer electronics device.

7. The system according to claim 1, wherein said first device further comprises:
   an optical for enlarging the perceived image at the consumer electronics device's normal focusing distance for sharpening the image independently at a distance at which is found the objective of the consumer electronics device used for acquiring the image; and
   a non-permanent connection for temporarily maintaining said first device in a functional position on the skin.

8. The system according to claim 1, wherein said first device further a visual information display that visually indicates in the image, the presence of a physical, chemical or biological characteristic of interest appreciated by the image processing.

9. The system according to claim 1, wherein said first device further comprising a visual information display which allows the user to add information to the area being imaged prior to imaging, the added information being exploited by image processing.

10. The system according to claim 1, wherein said first device further comprising a calibration information area for determining or correcting image elements, including to scale, color, distortions, aberrations from the acquired image of the skin.

11. The system according to claim 1, wherein said first device further comprising a window-like opening or a reflecting surface that allows specific active addition of light including a dedicated light source for illuminating the area of shooting.

12. The system according to claim 1, wherein said first device further comprising instructions or guidance on either using the device or for accessing the service, advices, advertising of a sponsor.

13. The system according to claim 1, wherein said first device is laid out so as to be delivered to the users in a form with small thickness using flexible materials so as to be able to be inset in a magazine or sent in an envelope.

14. The system according to claim 1, wherein the consumer electronics device allows the acquisition of a digital image containing the head of the person for whom at least one characteristic of the skin is desirably analyzed.

15. The system according to claim 1, wherein the consumer electronics device allows the system asking at least one question to the user.

16. The system according to claim 1, wherein the consumer electronics device allows the transmission of at least one piece of information to a remote server through a communication network.

17. The system according to claim 1, wherein the consumer electronics device allows the reception of at least one portion of the expected results from a remote server.

18. The system according to claim 17, wherein the said at least one portion of the expected results received from a remote server is a set of at least one cosmetic product proposed as being adapted to said at least one characteristic of the skin which was analyzed or relates to the latter.

19. The system according to claim 18, wherein the system allows the selection by the user of at least one product from the said proposed set of at least one cosmetic product.

20. The system according to claim 19, wherein the system allows a transaction in relation with the transfer of ownership of the at least one product selected by the user.

21. The system according to claim 20, wherein the system allows credit of a loyalty account.

22. The system according to claim 20, wherein the system allows launch of the manufacturing of at least one cosmetic product.

23. The system according to claim 17, wherein the said at least one portion of the expected results received from a remote server is the confirmation that no problem, or only minor problem have been detected during the skin analysis.

24. The system according to claim 17, wherein said at least one portion of the expected results comprising a list of dermatologists and/or hospitals comprising a dermatology department in proximity to the user localized beforehand in the case where a serious problem have been detected during the skin analysis or in the case of a doubt.

25. The system according to claim 24, wherein the system allows the making of an appointment.

26. The system according to claim 25, wherein the system allows the handling of priority depending on the urgency of the case.

27. The system according to claim 1, wherein the system the storage in one or more databases of information related to the user, including results of prior analysis, preferences through selections previously done in proposals, for promotional purposes and/or for pushing information of interest and/or for sending samples of products which may be attractive after testing, and/or for proposing other products which may be attractive according to said at least one product selected.

28. The system of claim 1, wherein,
   the consumer electronics device is one of the group consisting of a digital camera, a video camera, a webcam, a cell phone, a smartphone, a digital tablet, a phablet, a personal media player, electronic glasses, and a microcomputer;
   the optical magnification element is one of the group consisting of
   i) one lens,
   ii) a combination of lenses, and
   iii) a combination of at least one lens operatively connected to software executed in the consumer electronics device; and
   said digital image processing device is at least one of the group consisting of i) a usable calculation resource embedded in said consumer electronic device,
ii) at least one computer part of a local network, and
iii) at least one remote server in a frame of a cloud architecture;

said digital image processing device processes the received data of the acquired image according to at least one of the group consisting of i) image improvement including image correction through embedded references,
ii) skin characteristic extraction,
iii) additional visible information extraction and decoding, and
iv) image recognition including writing recognition, 2D or 3D code recognition, skin cancer recognition, recognition of typology relative to skin and/or hair in the image of a human head;

from the processed data, said digital image processing device produces the information in relation to at least one characteristic of the skin from the group consisting of i) a physical characteristic of the skin,
ii) a chemical characteristic of the skin,
iii) a biological characteristic of the skin; and the produced information from the digital image processing device comprises at least one of the group consisting of i) a result of skin or hair analysis suitable for a cosmetic purpose,
ii) a list of at least one cosmetic product adapted to the characteristics of skin or hair having been analyzed,
iii) a result of skin analysis suitable for a medical purpose,
iv) a result of screening of a disease including skin cancer,
v) at least one name/address for getting a medical consultation, and
vi) an appointment for a medical consultation.

29. The system of claim 1, further comprising:

a visual information display comprised in, or attached to the first device, said visual information display configured to include additional visible information in the acquired image of the skin to be further exploited by image processing, wherein, the consumer electronics device is a smartphone, the optical magnification element comprises a lens, said digital image processing device is a computer in communications with the smartphone over a network, said digital image processing device processes the received data of the acquired image according to one or more of the group consisting of i) image improvement including image correction through embedded references,
ii) skin characteristic extraction,
iii) additional visible information extraction and decoding, and
iv) image recognition including writing recognition, code recognition, skin cancer recognition, recognition of typology relative to at least one of the group consisting of skin and hair;

from the processed data, said digital image processing device produces the information in relation to at least one characteristic of the skin the group consisting of i) a physical characteristic of the skin,
ii) a chemical characteristic of the skin,
iii) a biological characteristic of the skin; and the produced information from the digital image processing device comprises at least one of the group consisting of i) a skin or hair analysis result suitable for a cosmetic purpose,
ii) a list of at least one cosmetic product adapted to the characteristics of skin or hair having been analyzed,
iii) a result of skin analysis suitable for a medical purpose, and
iv) a result of screening of a disease including skin cancer.

* * * * *